(12) United States Patent
Ala-Kleme et al.

(10) Patent No.: US 8,382,968 B2
(45) Date of Patent: Feb. 26, 2013

(54) CONDUCTOR/INSULATOR/POROUS FILM-DEVICE AND ITS USE WITH THE ELECTROCHEMILUMINESCENCE-BASED ANALYTICAL METHODS

(75) Inventors: Timo Väinö Kalevi Ala-Kleme, Mellilä (FI); Jarkko Uolevi Eskola, Turku (FI); Timo Kalevi Korpela, Turku (FI); Sakari Mikael Kulmala, Kirkkonummi (FI); Piia Kaarina Mäkinen, Kuusisto (FI)

(73) Assignee: Labmaster Ltd., Turku (FI)

( * ) Notice: Subject to any disclaimer, the term of this patent is extended or adjusted under 35 U.S.C. 154(b) by 1237 days.

(21) Appl. No.: 11/887,455

(22) PCT Filed: Mar. 30, 2006

(86) PCT No.: PCT/FI2006/000100
§ 371 (c)(1),
(2), (4) Date: Mar. 11, 2008

(87) PCT Pub. No.: WO2006/103313
PCT Pub. Date: Oct. 5, 2006

(65) Prior Publication Data
US 2009/0178924 A1    Jul. 16, 2009

(30) Foreign Application Priority Data

Mar. 30, 2005   (FI) .................................. 20050331

(51) Int. Cl.
   *G01N 33/561*   (2006.01)
(52) U.S. Cl. .................... 204/403.06; 422/53; 422/82.03
(58) Field of Classification Search .................. 204/291, 204/403.06; 205/131, 123, 80; 422/53, 82.05, 422/50; 436/172, 164, 6
See application file for complete search history.

(56) References Cited

U.S. PATENT DOCUMENTS

| | | | |
|---|---|---|---|
| 5,500,188 A * | 3/1996 | Hafeman et al. ......... | 204/403.01 |
| 6,251,690 B1 | 6/2001 | Kulmala et al. | |
| 6,645,776 B2 | 11/2003 | Kulmala et al. | |
| 2001/0021534 A1 | 9/2001 | Wohlstadter et al. | |
| 2002/0081749 A1 | 6/2002 | Kulmala et al. | |
| 2003/0192780 A1 | 10/2003 | Ala-Kleme et al. | |
| 2004/0086423 A1 | 5/2004 | Wohlstadter et al. | |
| 2004/0129579 A1 | 7/2004 | Crooks et al. | |

FOREIGN PATENT DOCUMENTS

| | | |
|---|---|---|
| JP | 9189662 A | 7/1997 |
| RU | 2089051 C1 | 8/1997 |
| WO | WO 03072752 | 9/2003 |

OTHER PUBLICATIONS

Finnish Search Report, Sep. 23, 2005.
International Search Report, Jul. 11, 2006.
Written Opinion of the International Searching Authority dated Jul. 11, 2006.
Translation of Decision on Grant for corresponding Russian Patent Application No. 2007139905, dated Sep. 29, 2009.

* cited by examiner

*Primary Examiner* — Alex Noguerola
*Assistant Examiner* — Gurpreet Kaur
(74) *Attorney, Agent, or Firm* — Buchanan Ingersoll & Rooney

(57) ABSTRACT

A conductor/insulator/porous film device is provided which is used in electrochemiluminescence methods and instrumentation based on the chemical excitation of label molecules with subsequent measurement of the luminescence in order to quantitate analyte concentrations especially in bioaffinity assays.

21 Claims, 22 Drawing Sheets

CONDUCTOR/INSULATOR/POROUS FILM-DEVICE AND ITS USE WITH THE ELECTROCHEMILUMINESCENCE-BASED ANALYTICAL METHODS

FIELD OF INVENTION

The present invention relates to analytical methods and devices exploiting the phenomenon of the electrochemiluminescence. The invention is especially suitable for quantitative bedside rapid diagnostics.

BACKGROUND OF INVENTION

Presently, there is a general burden need for fast, sensitive and quantitative diagnostic technologies. Such ones are suitable for wide market areas including public health, research, farming, environmental care, veterinary medicine, and certain industrial production areas. Improved sensitivity, speed, robustness, stability, and decreased cost per analysis are factors, which after being accomplished in diagnostic technologies, can find applications in quite new areas.

Very high sensitivity can be obtained with certain diagnostics instruments, but they are too expensive. On the other hand, certain methods can be enough inexpensive, exemplified by immunochromatography, but they are not applicable to certain needs of the market. Any technology, wherein a set of such demands are met, will have an important place in the future diagnostics and a huge market potential.

There is a number of different analytical principles in practical use in diagnostics: for example, assays based on radioactivity, enzyme-linked immunosorbent assay (ELISA), calorimetric assays, and assays based on fluorescence, and chemiluminescence including anodic as well as hot electron-induced (cathodic) electrochemiluminescence (ECL). The hot electron-induced ECL is described in detail in U.S. Pat. No. 6,251,690, Kulmala S., et al. Each of these techniques has their role as regards to the integral of sensitivity, robustness, stability, speed, and price. The differences between the techniques reflect the function of physical limitations or advantages of the methods. For example, a drawback of the application based on radioactive compound is the decay of the label within a period of time and the extra cost of radioactive waste from both the safety and environmental viewpoint. The application of the most sensitive assays on diagnostics is limited by the complicated nature of the tests and instruments, and only experts can perform the assays. The complexity of the assay is generally directly proportional to the price of the instrument and/or the test. In the context of complex instruments, it could be mentioned the anodic electrochemiluminescence techniques now becoming more and more popular: the instrument is a complicated laboratory robot, the handling of which needs expertise and where the measuring process involves repeated washes and preparative steps. They are factors that increase the cost of the analyses as well as increase the amount of waste and therefore will make this method impossible for the needs of small laboratories, doctors offices etc. (bedside or point of care analytics).

Commercially beneficial methods are based on the principle that the substances to be analyzed are identified and measured in mixtures by so-called label substances. In the measurements based on unique properties of biological molecules, as in immunochemical assays, the analyte to be measured (X) can be selectively sorbed from a mixture of molecules to solid-phase bound antibodies and then the bound molecules are measured with another labeled antibody selectively binding to (X). The label substances can be radioactive isotopes, enzymes, light absorbing, fluorescent or phosphorescent molecules, certain metal chelates etc., which are linked covalently to the antibody. Alternatively, the purified (X) can be marked and the amount of unknown unlabeled sample (X) can be measured by a competition reaction. The assays for DNA and RNA can be also based on the selective binding (bioaffinity). Also many other chemical and biochemical analyses can be carried out by the same principles. In order to decrease the cost and/or increase the measuring accuracy, there is presently a tendency to measure several different parameters at the same time in the sample. One possibility is to use labels fluoresceing or phosphoresceing (luminating) at different wavelength or possessing different fluorescence lifetimes. Different measuring principles and strategies, which can be used in immunodiagnostics, have been described in the book The Immunoassay Handbook, Edited by David Wild, Stockton Press Ltd., New York, 1994, on pages 1-618.

It is known in the prior art that organic substances and metal chelates are beneficial as label substances and that they can be excited by light or by electrochemically to produce luminescence specific to the label. These methods are particularly sensitive and are well suitable. However, because the measured concentrations are extremely low, there are also case-dependent difficulties; the use of fluorescence can be disturbed, among other things, by Tyndall, Rayleigh and Raman scattering. When measuring biological substances, there is, almost without exception, after the excitation pulse, a fast-discharging high background fluorescence. Phosphorescence in the solution phase can be utilized mostly only with chelates between lanthanide ions and specially synthesized organic molecules. The drawback of the excitation techniques with the photoluminescent labels is the complexity of the instruments and the high price of the sensitive optical components.

In general, the advantage of ECL is the low price of the electrical excitation components and simpler optics. Compared to the photoluminescence, several drawbacks can be avoided. Traditional anodic electrochemiluminescence with inert metal electrodes can be carried out with organic luminophores by a relative simple instrument in non-aqueous solvents. However, in bioaffinity assays, where the biggest commercial expectations are concentrated to, water solutions are applied. Biological samples are taken nearly always in non-organic solutions and therefore the measuring system should work in aqueous or at least in micellar water solutions. Only a very limited number of transitional metal chelates are working as ECL-labels in anodic ECL in water or micellar solutions.

Thus far the commercially most important analytical chemical application of the anodic ECL is the method using derivatives of $Ru(bpy)_3^{2+}$-chelate, where the detection phase of the label occurs in micellar phase. As known from textbooks, the micellar mixtures are always prone to different disturbing effects due to the uncontrolled complexity of the micellar equilibria. Thus, the hot electron-induced ECL, which does not depend on micelles has many crucial advantages over the anodic ECL. It can be applied both to immuno- and DNA hybridization methods (see, Blackburn, G., et al., 1991, Clin. Chem. 37: 1534-1539; Kenten, J., et al. 1992, Clin. Chem. 33: 873-879). The immunoassays and DNA or RNA probe applications by Roche Diagnostics Ltd. exploit magnetic particles by which the label substance is brought onto golden working electrode (Massey; Richard J., et al. U.S. Pat. No. 5,746,974; Leland; Jonathan K., et al. U.S. Pat. No. 5,705,402). The reproducible handling of magnetic latex particles is however in many ways difficult, therefore this method is useful only in expensive laboratory robots (e.g. Elecsys 1010 and 2010) having a complicated and precise liquid handling system. In addition, the permanent massive golden work electrode needs long cleaning and pretreatment between each analysis (Elecsys Service Manual, p. 70).

Although in many respect superb, a drawback in the hot electron-induced ECL in bioaffinity assays is the need of long incubation time in order to get the reacting molecules into equilibrium, which is necessary to optimize the analytical accuracy. According to the present invention, a significant improvement in the performance can be acquired with placing a thin porous film on the work electrode, termed here later on as CIPF-device, as described in the claims 1-10.

BRIEF DESCRIPTION OF DRAWINGS

FIG. 3. Measuring cell structures of a luminescence reader.

FIG. 5. Disposable measuring cell fitted to the test strip.

FIG. 7. A test strip, where all needed reagents are ready in dry form and where the starting and the stopping of analysis reaction are controlled.

FIG. 19.

DETAILED DESCRIPTION OF THE INVENTION

Figure 1:
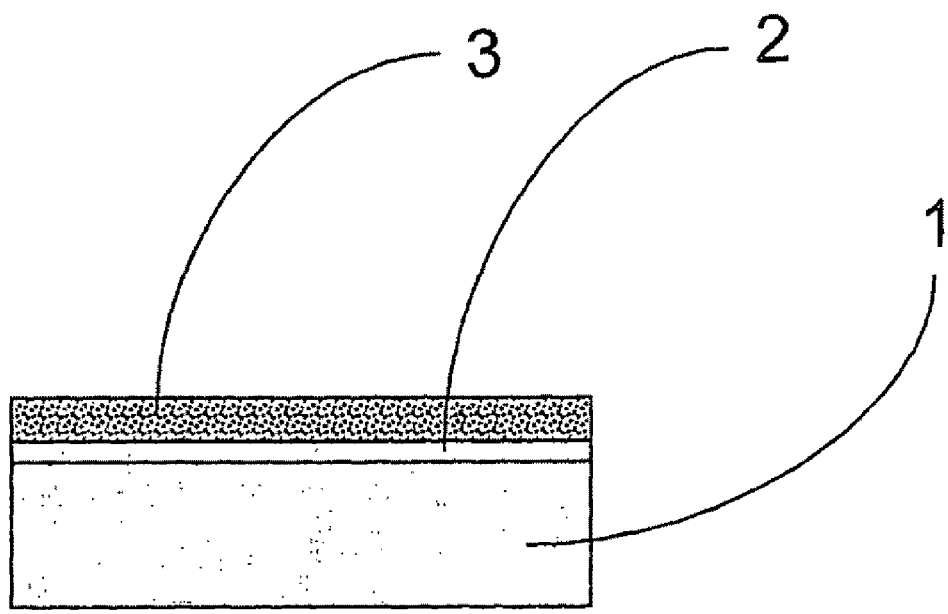
FIG. 1. A schematic diagram of the conductor/insulator/porous film-device (CIPF) according to the invention. Electrode structures can contain conductor (1), insulator (2) and porous film (3). The structure is termed CIPF.
Figure 2A:
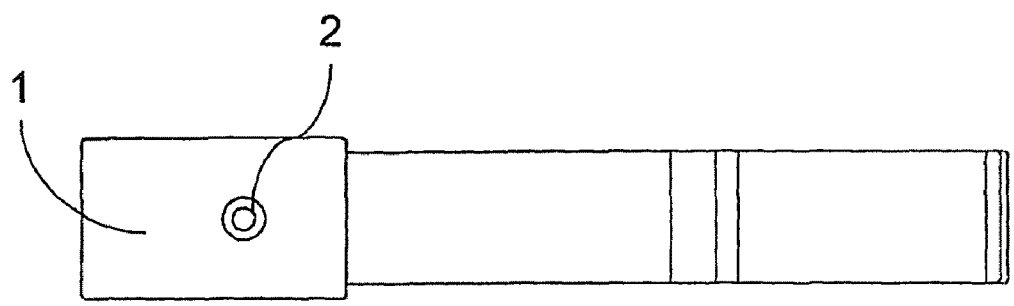
FIG. 2. One practical way to construct a test strip for the cathodic ECL-reader according to CIPF-principle. The hot electrons are injected through silicon (Si) chip covered by an insulating film. The Figure also shows the porous film attached to a sliding sledge over. The structure of the sliding lid and the test strip is constructed so that in the low position the porous film is attached to the surface of Si chip. When the lid slides upwards the porous film rises out off the surface of the cathode and takes place again against the arm part in the up position. An example of test strip structure (FIG. 2). The test strip contains a moving lid (1) what when it moves along the arm (3) will rise up (9) and will lock in its place at the very end of the arm. The sample to be analyzed is added through the opening (2). The porous film (5) is located under the opening and the film lies against the Si electrode (6) with spikes (8). Under the silicon, there is a metal conductor (7), wherefrom a connection (4) to outer current source exists.
Figure 2B:
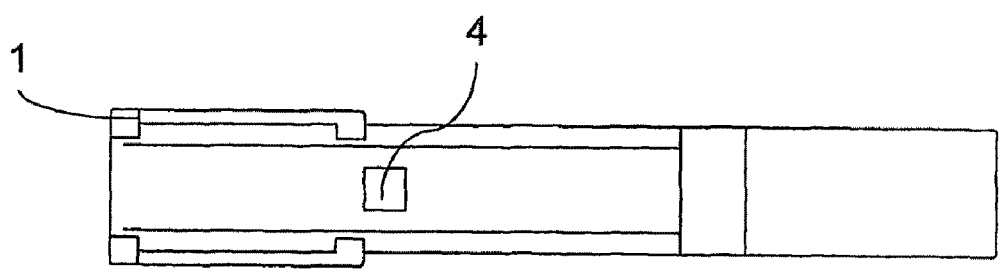
Figure 2C:
Figure 2D:
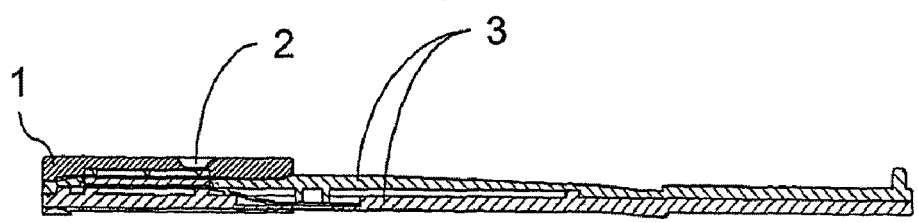
Figure 2E:
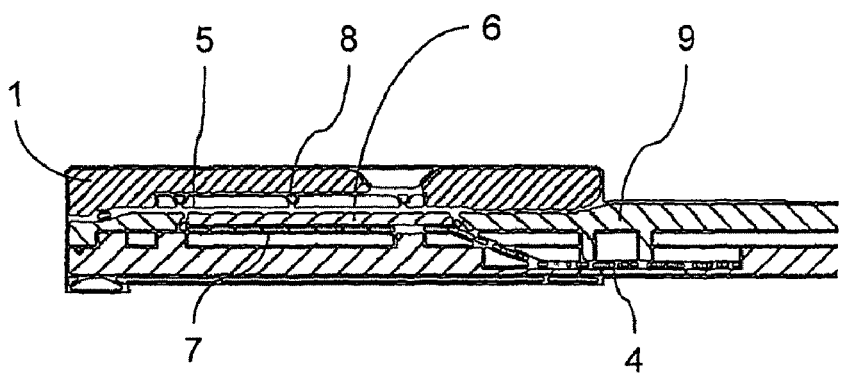

According to the present invention, different analyses can be performed with simple and inexpensive devices equally well as with complicated devices described in the before, whenever the actual immunoassay or DNA hybridization is done with the porous film on the surface of working electrode (CIPF-device). Then the measuring device and the measuring cell are cheap enough for the needs of the bed side analytics.

The porous film means in this invention a porous liquid-permeating film having thickness less than 100 µm, which is set over ECL cathode. The cathodic ECL electrode, unlike the anodic ECL electrode, functions distinctly differently from the conventional electrochemistry because the cathode carries on its surface a thin insulating film according to the U.S. Pat. No. 6,645,776 B (Kulmala et al.) The porous film lies over the insulating film of said cathode. The electrode according to the invention contains therefore at least two films, one electrically nonconductive insulating film and over it a porous film with thickness less than 100 µm. The porous film is electrolytically conductive unlike said insulating film. The porous film is therefore distinctly different from the electrode material described in U.S. Pat. No. 6,645,776B. In the anodic ECL applications (U.S. Pat. No. 4,280,815A, Technicon; U.S. Pat. No. 5,324,457A, Univ Texas Instruments; U.S. Pat. No. 6,090,545A, Meso Scale Technologies) have earlier applied different porous materials as an electrode itself or as a coat of the electrode. The object of the porous materials in said inventions has not been, however, similar as in the present invention. Because the cathodic ECL functions on different electrochemical principle than the anodic ECL (among other things, the distance of excitation zone from the electrode is different), the porous film itself in the present invention never works as an electrode. By setting the porous film over the electrode, there will be found new surprising properties compared to the prior art technologies. Furthermore, an uniform sample layer can be spread quickly by the porous film over the cathode.

The present invention discloses the conductor/insulator/porous film-device (CIPF) especially in the context of the cathodic ECL. Very different kind of labels can be excited with it as exemplified in FIG. 8. The principle of CIPF-device is described in FIG. 1. The device is put into the operative state by adding a liquid sample or buffer for getting a liquid contact onto the porous film, wherefrom the sample or buffer spreads over the whole working electrode. The device was found to work as a surprisingly fast immunoassay system. Suprisingly it was also found that labels could be excited in the distance of below 100 µm in the porous film. According to the present invention, inexpensive disposable working electrode containing CIPF-devices, -sensors or -probes can be produced and hence traditional working electrodes of ECL can be replaced by disposable working electrodes. Simultaneously, the cleaning and equilibrium operation necessitating the sophisticated robotics for handling of microparticles, for example, can be avoided.

This invention forms a significant improvement over the prior art to devices and methods intended onto POC markets by making possible manufacturing of cheap quantitative rapid tests. This is accomplished by combining the ECL mechanism and measuring principle with different thin porous films.

It is known in the prior art that different porous materials can be used for liquid transport and filtering in assays based on immunochromatography (Hybritech Inc., see Clinical Chemistry 31 (1985) 1427). These methods, however, are not quantitative and they are not used in the context of the cathodic ECL, the principle of which is totally different from those of traditional electrochemistry.

In microfluidistic systems or in methods using microliter volume sizes, there are often problems of air bubbles, harmful effects of heat diffusion, problems caused by laminar flow, that is, unmixing of liquids within the flow, and surface forces caused by capillary phenomena. In this invention, there is demonstrated a novel way to employ thin porous films, not only for filtration but also as a homogenic equalizer and spreader of liquid flow. This is possible to do especially easily with the smooth silicon electrodes of the electron-induced ECL. Moreover, the CIPF-device simplificates drastically the whole blood sampling and handling processes in assays done by ECL detection method and instruments. By using the porous films in these microfluidistic methods several drawbacks of the prior art can be totally eliminated or significantly decreased.

The invention comprises an equipment by which analytes and other reagents are spread over the ECL working electrode followed by electric excitation in such a way that the working electrode assembly can be used as a rapid test device based on immunoassays and DNA probe methods.

The goal of the invention was reached by using CIPF-devices with thin porous films with thickness less than 100 µm as homogenic equalizer of liquid flows and as a spreader of the liquid of micro flow-through cells or micro layer cells in on ECL-based detection methods of the bioaffinity assays, wherein is the characteristics of the device are as described in claims 1-10. This invention focuses especially to the methods and devices by which the cathodic ECL can be performed in practice. In addition, it is especially characteristic to the invention that the cathodic excitation occurs in the proximity of the electrode (the proximity assay principle). The assisting porous film can be placed tightly to the electrode, which is not possible in other detection methods. Alternatively, the porous film can be brought to the electrode in order to start the bioaffinity reaction and later taken off before the measurement of ECL. The measurement can be done, however, also directly through certain porous films. The label substance can be dried onto the porous film placed to the electrode or onto to surface of the working electrode. The liquid junction between porous film and the working electrode is optimally less than 100 µm. The porous film can be bound covalently or by adsorption directly to the surfaces by methods known in the prior art (e.g. in product of Schleicher & Schuell Ltd.) but not in the context of their use in ECL.

The main embodiment of the invention is the ECL working electrode. The electrode material in hot electron-induced ECL is a conductor covered by a thin insulating film, whose material can be Al or Si according to the U.S. Pat. No. 6,251,690 (Kulmala et al.). Most preferably it is flat silicon which is oxidized so that it is covered by an insulating film with thickness of 1-10 nm, most preferable insulating film with thickness of 3-4 nm. Silicon substrate can, however, be channeled or otherwise the surface morphology can be modified in order to improve the liquid flow or its electrical properties. The size of the silicon chip can vary depending on the intended use and whether it is meant to measure one or several analytes in the same time. Typically the size of the silicon chip is 4×9 mm and thickness less than 1 mm. The silicon chip is attached to a supporting structure, which can have different shapes depending on the size and material requirements of the measuring instrument in use. Typically the supporting structure is made of plastic, which is environmentally friendly and easy to dispose. Depending on the film properties the porous film is spread as wet or dry over the silicon chip placed to the surface of the supporting structure.

It is characteristic to the porous films placed to the surface of the electrode of the invention that they are microporous and the thicknesses are less than 100 µm. Materials according to the invention are available from several commercial sources like Millipore, MSI, Sartorius, Pall, Sigma and DuPont. The porous films can be either isotropical or anisotropical. The production technologies vary and they can involve compression or stretching, the pores can be done by chemical or physical means or in case of anisotropical porous films by phase transfer. Also the sintering of microparticles can be used. Suitable materials of porous films can be chosen, but not limited to, among PTFE, polyvinyldienefluoride, polycarbonate, polysulphone, nylon and cellulose esters. Such films and others are available from commercial sources with different pore sizes and thicknesses and different physicochemical properties. Among the useful fiber materials, glass fiber, filter paper, and filter textiles can be mentioned.

The use of porous films in CIPF-devices gives significant advantages over the prior art for bioaffinity assays. With porous films the sample can be spread equally over the antibody-coated working electrode. The porous films worked unexpectedly as homogenic equalizer of liquid flows and prevention of formation of bubbles in microfluidic systems (special problem of ECL), heat diffusion, unwanted effects of surface forces and laminar flows, and thus eliminated problems in the microfluidic micro flow-through cells or in microlayer cells.

In the case that the porous film is enough thin, less than 100 µm in the ECL-based bioaffinity assays, the reacting compounds can be also brought to the porous film placed over the electrode so, that the porous film is in a liquid contact to the surface of the electrode. Against theoretical considerations (see, U.S. Pat. No. 6,251,690, Kulmala S., et al. and other publications), according to the present invention, the excitation pulses from the electrode can excite label molecules in the porous film at significantly longer distance from electrodes than expected thus far, i.e. in the porous film of thickness less than 100 µm.

The surface of the electrode can be coated by known means with antibody or DNA and the bound label molecules excited with electrical pulses. In this case the porous film, used to spread sample and reagents, can be removed, whenever desired, before the measurement.

Patient sample (plasma, serum, whole blood, cerebral fluid, urine etc.) can also be taken to the porous film, dried and stored on it. This can be an exceptional advantage of the present invention, for example in order to make easier the transportation of the samples. The porous film containing the sample can be inserted so as to be as the normal functioning part of the CIPF-device and the concentration of the analyte measured as described elsewhere in the context of the present invention.

The surface of the electrode or of the porous film to be placed against, can be coated with antibodies or antigens by the earlier known methods allowing high density of active antigens or antibodies on the surface. According to the present invention the electrodes or the surface of the porous film to be placed against the electrode can be coated by Langmuir-Blodgett films described in the Examples.

It is advantageous for productional reasons to store the CIPF-devices dry. Then the devices are brought up to functional condition only by adding liquid sample or buffer solution to the surface of the porous film enabling suitable conditions bioaffinity reactions between the porous film and the electrode.

The CIPF-device described in the invention can comprise, in addition to the supporting structure, porous film, and electrode (CIPF), include other parts and shields making the device more practical in usage. If analytes are measured from whole blood, the removal of blood cells can also be done by specific porous films as shown in the Examples. The device according to this invention contain also electrical connection from working electrode to the excitation and luminescence measuring operations. It is typical to the CIPF-device that a large number them can be produced by automated production lines. The production methods of the different individual components of CIPF-device and their assembling to get the device are basically known in the prior art.

Smooth surfaces are preferably used as the electrode materials of the present invention. The quality of coating of the electrodes with bioaffinity materials is crucial for the function of the CIPF devices. The quality control can be based, therefore, directly on the extremely accurate tunneling and/or atomic force microscopy. This can be done by the direct observation of e.g. active coated antibodies, what in practice is impossible with other types of diagnostic methods and therefore the possibility of the quality control is one of the central strengths of this invention and in this way the most central quality criterion of the diagnostic methods will be fulfilled. The generally used coating of polystyrene with antibodies does not have the possibility to this kind of control because the surface of polystyrene after injection molding is too rough for the identification of the molecules on the surface of the material.

The quantitative rapid tests and the preceding steps of determinations like e.g. the needed pretreatment of whole blood samples can be considerable simplified with the methods and devices shown in this invention. E.g. the clotting of the whole blood sample preventing heparin treatment is not necessary in the method. The porous film to spread the analyte also excludes blood cells from contact to electrode and the porous film with the blood cells can be readily removed leaving the bioaffinity coated electrode exposed. Naturally also heparin treated whole blood samples can be measured with this device and method.

The working electrode (in cathodic ECL Al, Si etc.) or the thin porous film over the working electrode in question can be coated with antibodies. If the porous film is coated with antibody/antigen/RNA/DNA the measurement will be done without removing the porous film, but if the working electrode is coated with the analytes recognizing biomolecule the porous film can also be removed before ECL-measuring step. The ECL-measurement of the present invention is preferably carried out with the hot electron-induced electrochemiluminescence (U.S. Pat. No. 6,251,690).

There are several alternative approaches for the CIPF-devices according to the invention depending on the intended application. According to the present invention, there is a typical separate test strip, whereto analyte is added. Sample is spread by the porous film to the surface of antibody-coated piece of silicon electrode. The sample dissolves the labeled bioaffinity molecule dried on the porous film. The porous film can be attached with a tape to the sliding lid part, which is over the working electrode during the pipeting step of the sample and during incubation time followed by sliding away before washing and measuring step. There is an opening with size of the working electrode in the tape, so that the porous film is sticked with tape only from the edges. When the sample has been added to the sample hole, the porous-film dried labeled antibody dissolves and the immunoreaction starts on the surface of the antibody-coated working electrode. The porous film works as a homogenic spreader of the liquid. It also prevents the problems caused by the air bubbles and also eliminates other above problems in microfluidic systems. The test strip is transferred into the measuring device, where the bioaffinity reaction is accomplished with or without shaking. The shaking is done by the electric vibration motor attached to the body of the instruments measuring cell or a turbulence is achieved by other means in the instrument. After the equilibrium is attained to the wanted degree, the test strip is transferred into the measuring cell and at the same time the thin porous film over the working electrode slides up when the working electrode is exposed for wash and measurement. In the ECL-system, the counter electrode can be an integral part of the measuring cell. The volume of the measuring cell can be 50-500 μL. The heterogeneous bioaffinity/immunoassays involve the washing step of the test strip but in homogeneous assays only ECL-measurement. The composition of washing and measuring solutions can be the same. The washing can be performed by filling and aspirating the measuring cell. The transport of the solutions can be implemented in the measuring instrument by a pump. After the measurements, the cell shall be rinsed. A valve in the instrument controls if there is a flow into the cell of washing/measuring buffer or distilled water. Simpler portable rapid test ECL instruments do not involve liquid handling by the instrument but due solution containers are involved in the disposable test strip itself.

The ECL-measurement of a bioaffinity assay, wherein a thin porous film (e.g. nitrocellulose) is coated/impregnated with antibody, can also be performed with the CIPF-device principle but then a modified measuring cell and test strip is needed compared to the above-described model (film reaction device). Because expressly the reactions take place in the porous film, the test strip is constructed so that there is an open lid for the washing arrangement of the porous film and measuring cell of bigger size, where the test strip can be inserted to.

The above-described film-reaction construction of the CIPF-device can also be applied to more complicated laboratory equipments. The working electrode can be attached to a cell, like to a micro flow-through cell, and the anode can be one-side conductive material-coated material like. ZnO glass or ITO film or the structure of the anode can be net-like, exemplified by a steel net or only thin steel wire. The porous film is locates between the electrodes as free or fixed. Because the porous film and the over it tightly attached counter electrode exceed the length of the working electrode, will the flow trough the cell be accomplished by connecting the flow tubings or miroliter size pipeting containers to the perforated counter electrode. Alternatively, the whole CIPF-device or sensor can be moulded inside liquid flow channels in plastic equipped with connectors to sample and wash injections. The device construction can also include anodic counter electrodes around the cathodic working electrode. Also then most favorable way of spreading the solution of (sample, label and wash) is the porous film between the electrodes in the case of heterogeneous assay. Also homogeneous assays can be performed with the similar method and device because the washings are not necessary. This is based on the fact that cathodic ECL excites only the labels concentrated by the bioaffinity reaction to the surface of the electrode (so-called proximity effect).

The label reagents can be dried onto the porous film. For drying bioaffinity labels, the porous film material can be any porous film with thickness less than 100 μm exemplified by polycarbonate or nitrocellulose. For the quality control of the coating of the working electrodes it is favorable to use atomic force microscopy (AFM). The working electrodes can be coated with antibodies by physical adsorption or by covalentic binding and also by the extent of the order of the antibody-surfaces increasing Langmuir-Blodget (LB)-film and Langmuir-Shaefer methods.

Next the invention will be clarified further by diagrams and non-limiting examples and figures linked to them.

Example 1

Preparation of the Insulating Film-Coated Electrodes from Si-Wafers by Thermal Oxidization, Slicing and Coating with Antibody The oxidation of Si wafers. The wafers (Si wafers: resistivity 0.01-0.023 Ωcm, p++ boron-doped, orientation <100>, thickness 525+/−25 μm, producer Okmetic Oyj) were washed the RCA washing generally used in industry and were placed into an oven at 700° C., where the atmosphere contained 95% nitrogen, and 5% oxygen. The temperature was increased to 850° C. and oxygen partial pressure was increased: 90% nitrogen, 10% oxygen and incubated for the desired time. The wafers were rinsed with pure nitrogen flow for 30 min. The temperature was degreased back to 700° C. in pure nitrogen and the wafers were removed from the oven.

The following results were obtained with different oxidation times:

| Oxidation time (min) | Thickness (nm) |
| --- | --- |
| 0 (*) | 2.666 |
| 15 | 3.418 |
| 30 | 3.936 |
| 40 | 4.171 |
| 60 | 4.852 |
| 80 | 5.535 |
| 120 | 6.393 |
| 200 | 8.070 |
| 400 | 11.442 |

The thickness was measured by an ellipsometer by the polarization change of a laser beam. In the method with thin films the refractive index is fixed and a typical value of 1.465 is used for the oxide. A surface protective tape was fixed to the unpolished side of Si wafer. The wafer to be sliced was attached to slicing base and was sliced by computer controlled diamond blade saw into needed size of Si sensor preforms.

Figure 9:
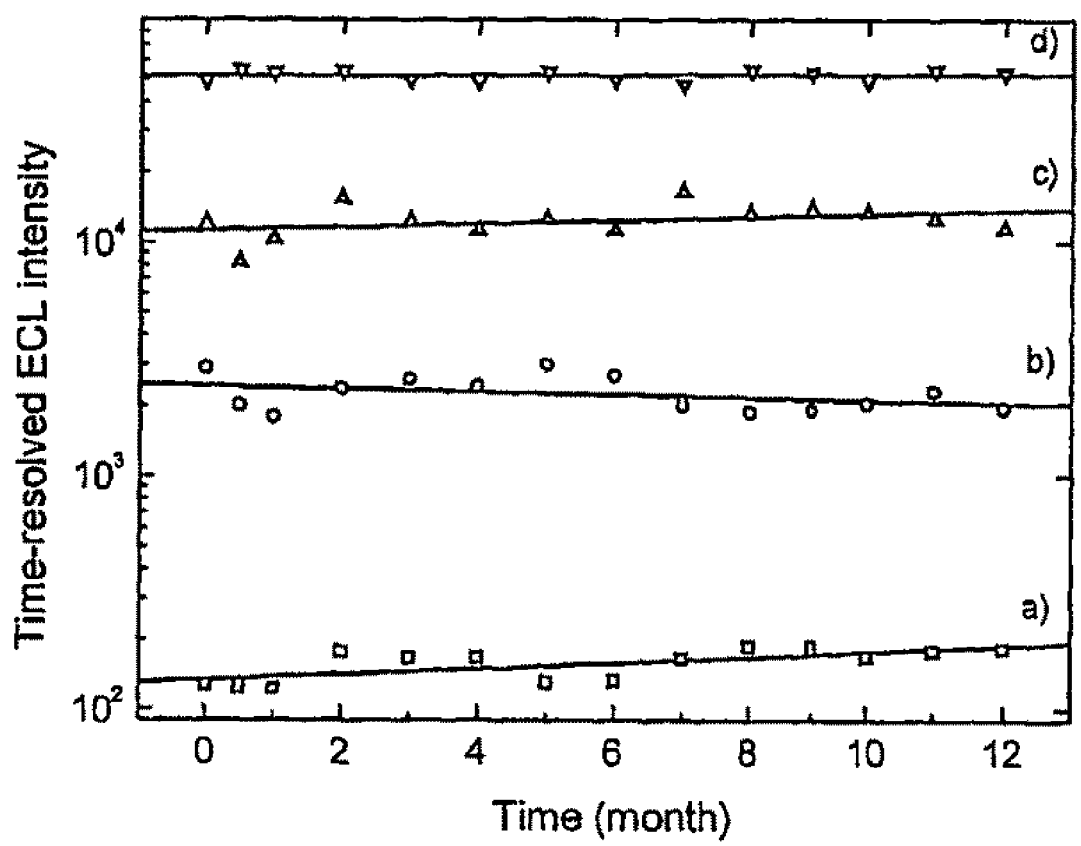
FIG. 9. Stability of Si-chips during one year as measured by heterogenic hCRP immunoassay, with the CIPF-device and luminescence reader. CRP concentrations were (a) 0, (b) 10, (c) 30 and (d) 100 ng/mL.
Figure 10:
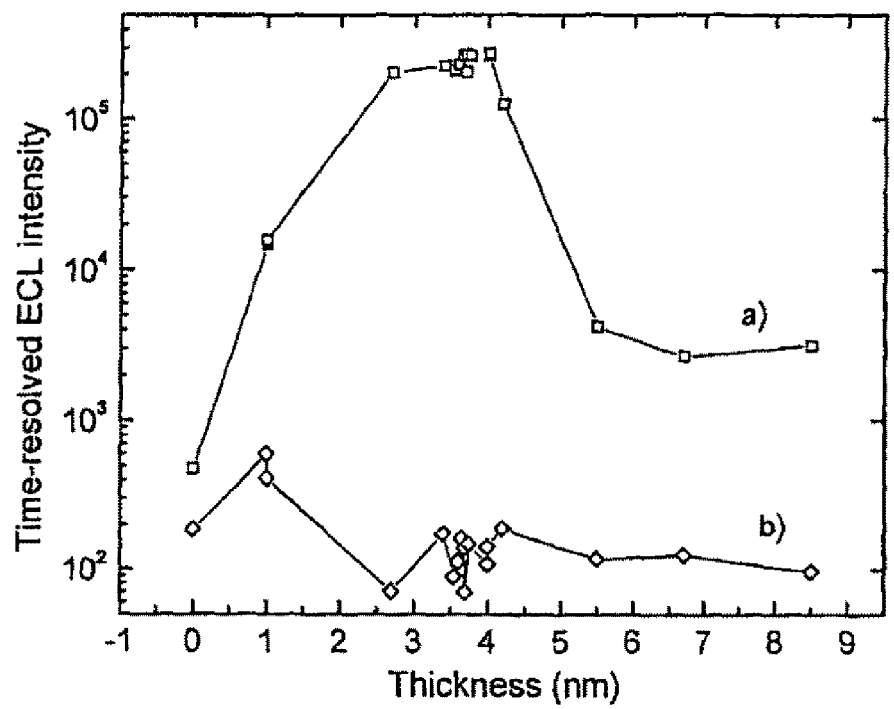
FIG. 10. The effect of the thickness of the oxide layer of Si chips with cathodic ECL, (a) $10^{-7}$ M Tb(III) chelated with 2,6-bis[N,N-bis(carboksymethyl)aminomethyl]-4-bentsoylphenol (b) control solution (measuring buffer).
Figure 11:
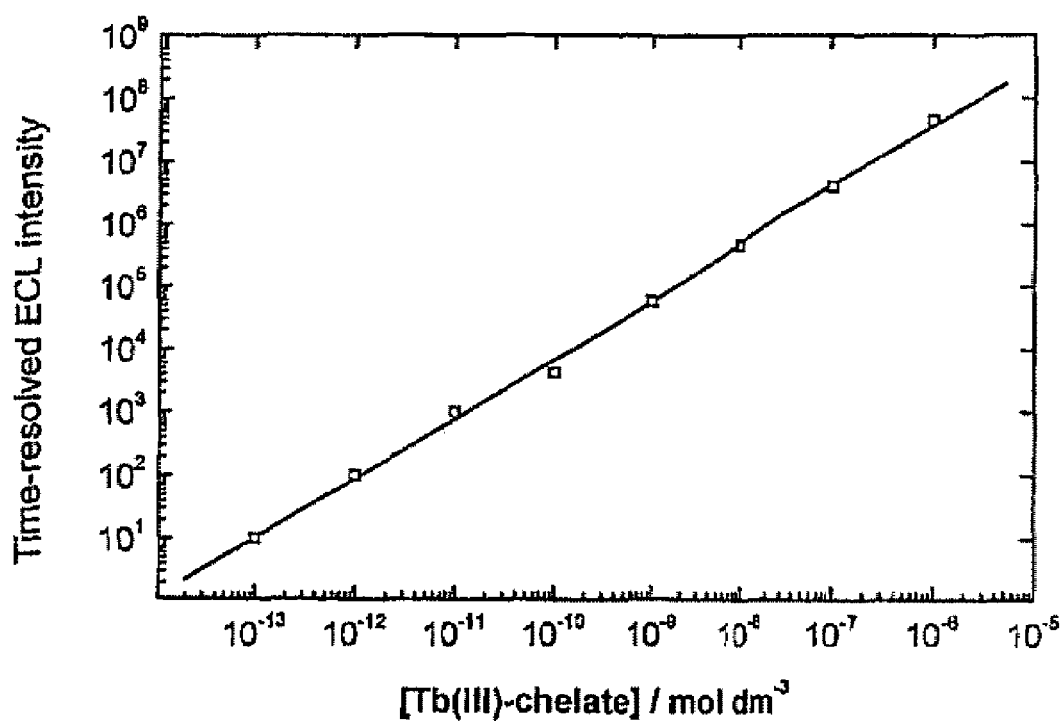
FIG. 11. Calibration curve of label luminophore of pure terbium 2,6-bis[N,N-bis(carboksymethyl)aminomethyl]-4-bentsoylphenol chelate as measured with ECL reader and test strip (CIPF). The measuring cell was filled with measuring buffer and label luminophore.
Figure 12:
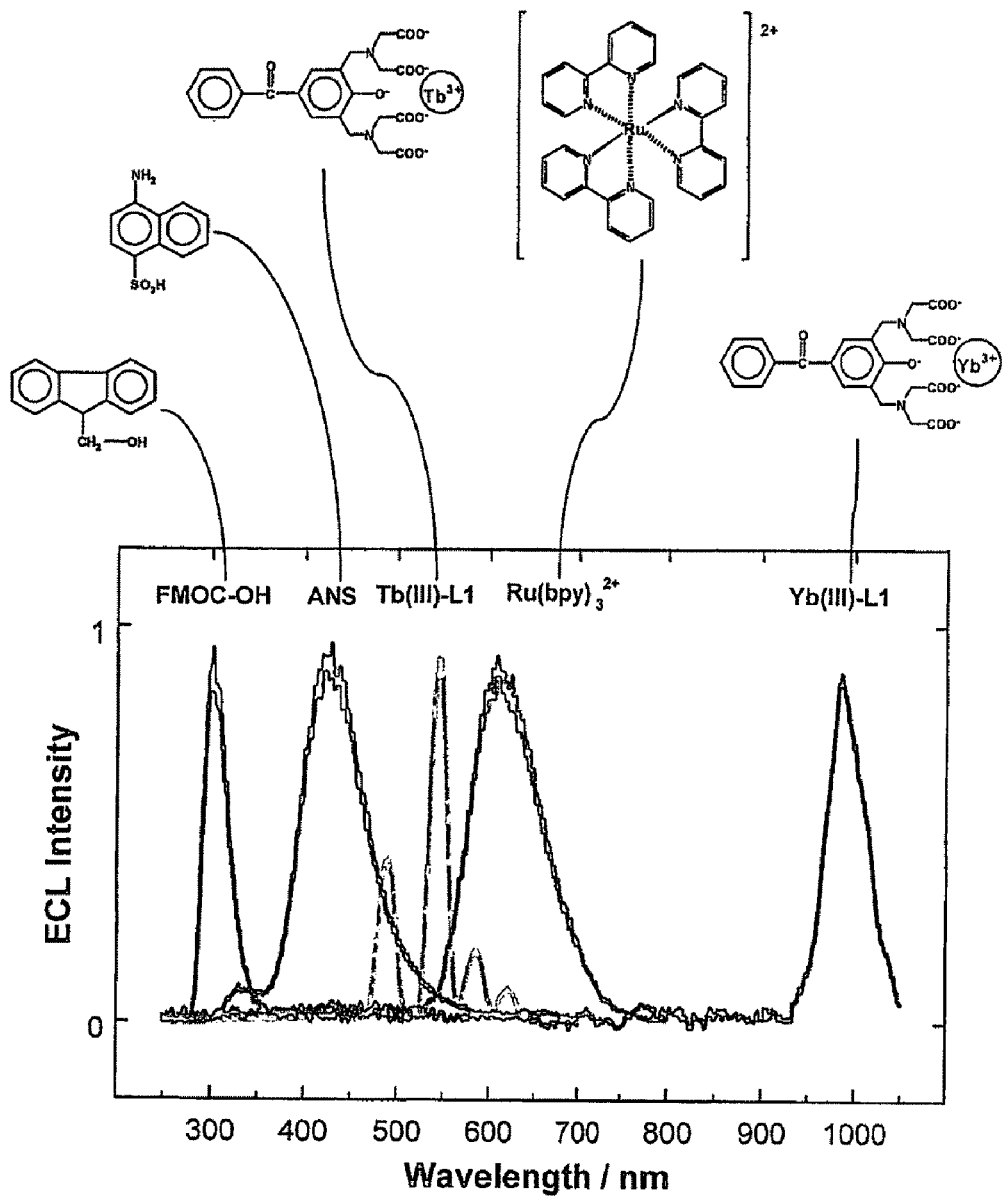
FIG. 12. Structures and ECL spectra of different luminophores suitable for labeling of an antibody (ANS 4-amino-1-naphthalenesulfonate, FMOC-OH=hydrolyzed 9-fluorenylimethyl chloroformate, Tb(III)-L1=Tb(III)-chelated by 2,6-bis[N,N-bis(karboxymethyl)aminomethyl]-4-bentzoylphenol, Ru(bpy)32+=rutenium(II) tris-(2,2'-bipyridine chelate, Yb(III)-L1=Yb(III)-chelated 2,6-bis[N,N-bis(karboxymethy)aminomethyl]-4-bentsoylphenol). It can be concluded that the whole UV-VIS-NIR spectral area is operative. The measurements were done with a CIPF-device and luminescence reader.

The antibody coating can be carried out, for example, so that the sliced, but still to the protective tape-bound Si wafer will be placed the polished side downwards to float on the coating solution in a plastic bowl (coating solution: 50 mM Trizma base, 0.05% $NaN_3$, 0.9% NaCl, pH 7.8 with HCl, containing anti-CRP antibody 7.0 μg/mL; Medix Biochemica Oy Ab anti-hCRP clone 6405, 1.0 mg/ml). Coating volume was 50 mL/wafer or 4.5 μg antibody/$cm^2$. The coating was allowed to proceed over night in humid space and thereafter the wafer was transferred into a new saturation solution (50 mM Trizma base, 0.05% $NaN_3$, 0.9% NaCl, 0.1% BSA, 6% D-sorbitol, 1 mM $CaCl_2*H_2O$, pH 7.8 with HCl)-containing bowl and the saturation was allowed to proceed over night. For storing, the sliced and coated ready-made Si sensors-containing plates were dried at 30° C. for 2.5 h and were placed thereafter air-tightly with drying substance into a refrigerator. When the test strips are assembled, the Si slices are taken from storage, protective tape is removed attached to the test strip (FIG. 2). FIG. 9. shows the storage stability of the antibody-coated CIPF-devices. The effect of the thickness of the oxide layer on the ECL signal is presented in FIG. 10. FIG. 11 shows the concentration dependence of terbium-2,6-bis [N,N-bis(carboksymethyl)aminomethyl]-4-bentsoylphenol chelate label, as measured free in solution phase. FIG. 12 shows spectra of different useful label luminophores demonstrating that the whole spectral area (UV-VIS-NIR) can be used with cathodic ECL device and method.

Example 2

Heterogeneous CRP Immunoassay Exemplified with Standard Solutions and the Test Strip and Measuring Cell in Accordance with FIGS. 1 and 2

Figures 3A, 3B:
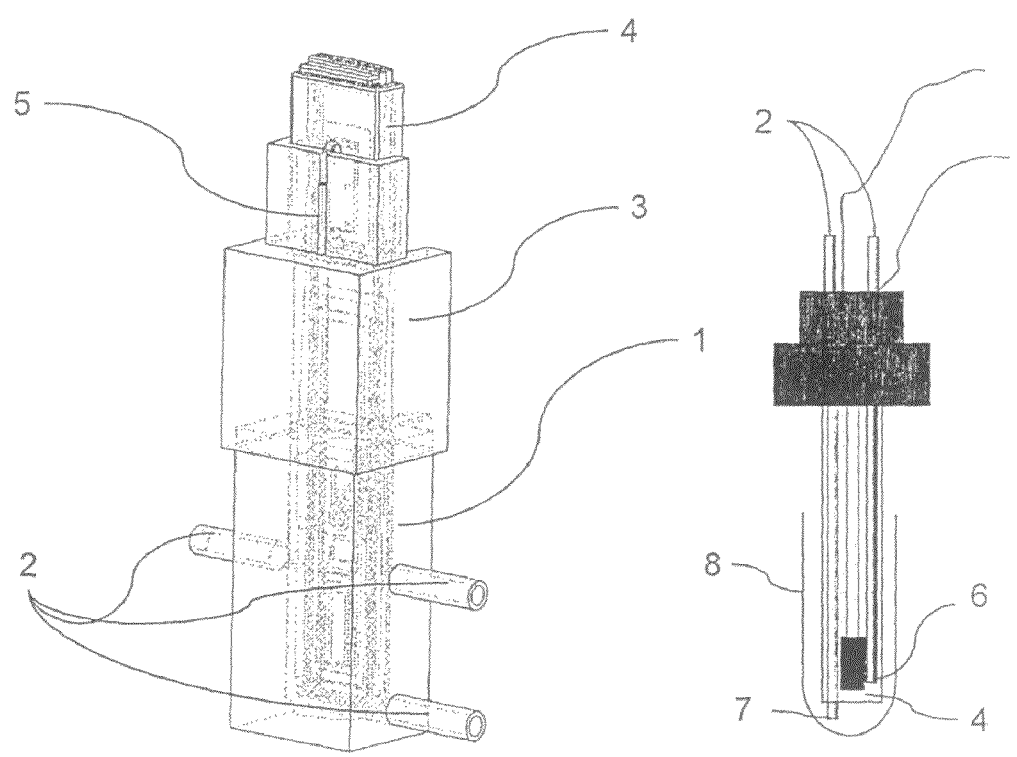
FIG. 3A: the test strip (4) in the cell (1) is in the measuring position. A shaking motor (3) is connected to the upper part of the cell also including contact (5) in test strip for electrical excitation. The washing is arranged through connectors (2).
FIG. 3B: the measuring cell (8) has disposable construction. The washing is arranged through connectors (2). The washing/measuring solution is brought into the measuring cell through conducive steel pipe (6), which works also as anode. The aspiration of the solution is carried out by another pipe (7). The electrical contacts of the test strip (4) are located in the upper part of the strip.

The CRP immunoassays were performed with Si-chips prepared according to Example 1. The construction of the test strips was as in FIG. 1 and FIG. 2. The sliding porous film-containing test strips were measured with the cell and device as shown in FIG. 3A. The immunoassay was based on the use of porous films combined with the ECL detection. Alternatively, by slightly modifying the test strip, it was possible to perform the measurement with the disposable measuring cell described in FIG. 3B.

Porous film attached to the sliding lid part of the test strip contained dried label. The polycarbonate porous film of outside measure of 7.00×12.0 mm (thickness 6-11 um, $1×10^5$-$6×10^8$ holes/$cm^2$, Whatman) was inserted to the tape frame of the same size (3M 465, two-sided acryl tape without backing material) having an opening of the size of Si chip 4.00×9.00 mm. Drying of the label to the porous film was as follows. The labeled antibody (Medix Biochemica Oy Ab anti-hCRP clone 6404, 2.22 mg/ml) containing solution (50 mM Trizma base, 0.05% $NaN_3$, 0.9% NaCl, 0.5% BSA, 0.05% bovine gamma-globulin, 0.01% Tween 20, 1 mM $CaCl_2*H_2O$, pH 7.7 with HCl, containing with Tb-2,6-bis[N,N-bis(carboksymethyl) aminomethyl]4-bentsoylphenol-chealate labeled antibody 0.074 mg/ml) was pipetted (0.5 μL) and dried as a drop with diameter of 2 mm onto the center of the porous film (12.0× 7.00 mm). The drying was allowed to proceed at room temperature overnight.

Figure 4:
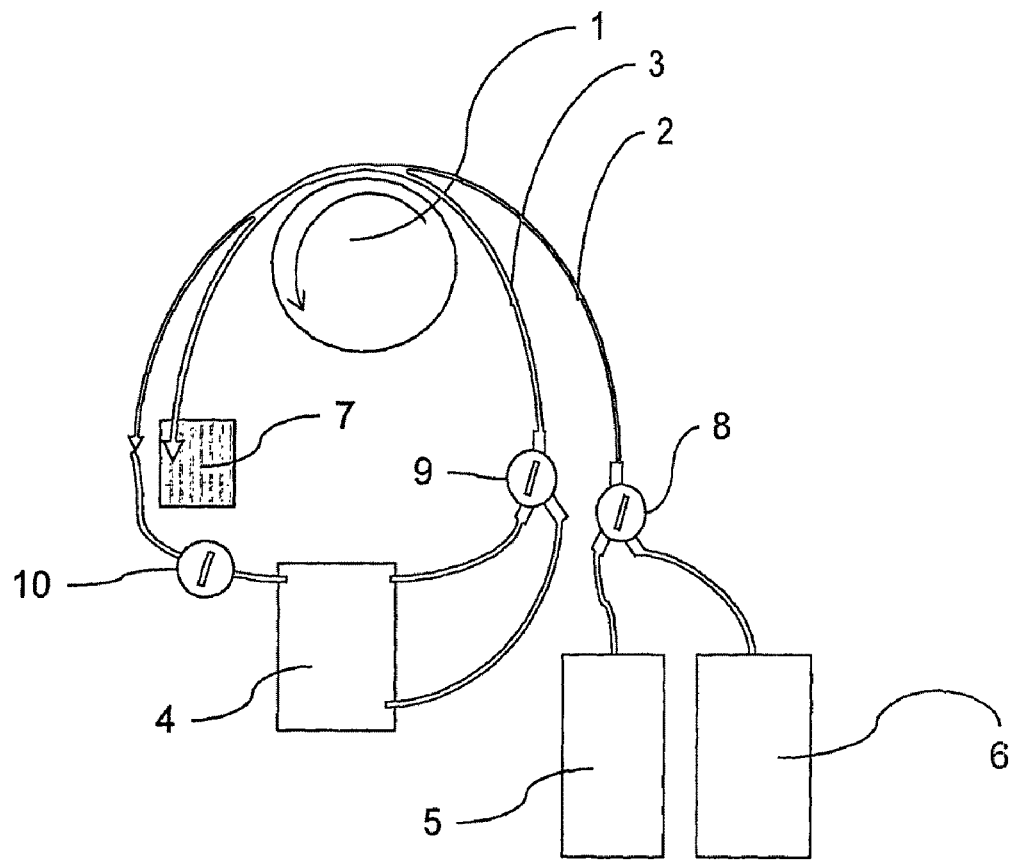
FIG. 4. Assembly of a wash system of the measuring cell. A peristaltic pump (1) transfers wash solution (5) through the tubing (2) into the cell (4). The same peristaltic pump aspirates from the upper part of the cell through another tubing (3) with higher suction efficiency than the other one (2). Valve (9) selects the aspiration of the cell from bottom or top part. When the valve (10) of the thinner tubing is closed, the cell can be drained from the bottom of the cell. When needed the cell can be washed (6) by adjusting the valve (8).
Figure 13:
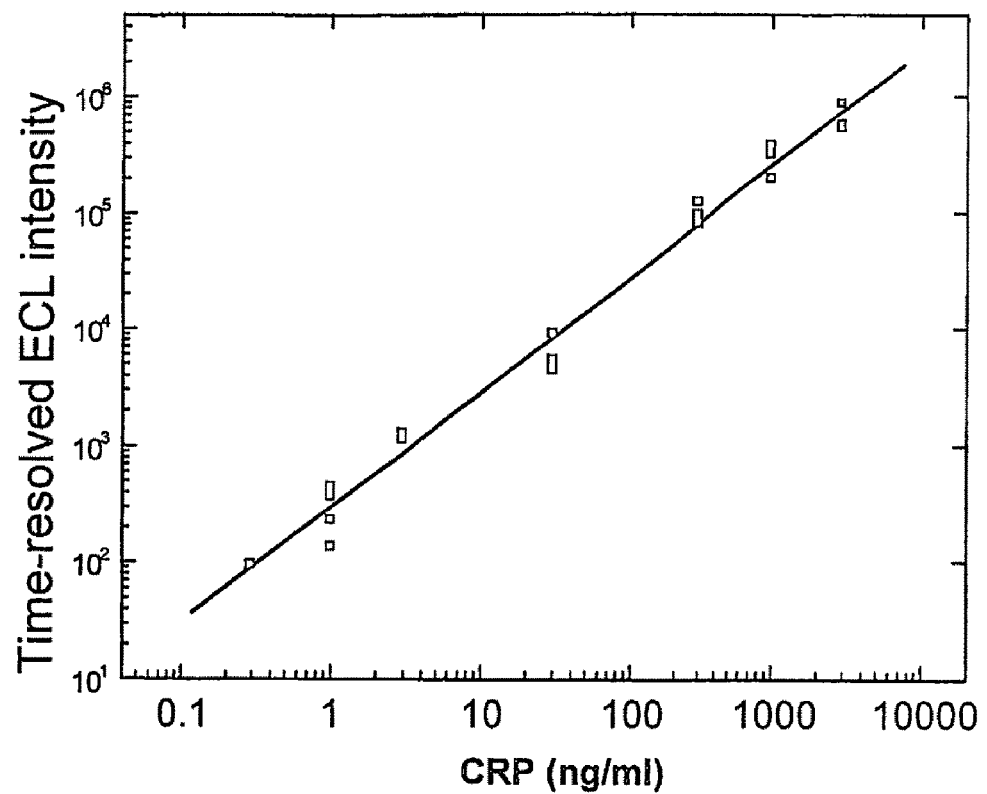
FIG. 13. Calibration curve of heterogenic hCRP immunoassay (see Example 2).

The immunoassay standard samples (CRP concentrations 0.3, 1.0, 3.0, 10.0, 30.0, 100.0, 300.0, 1000.0, 3000.0 ng/ml) were prepared in a test tube by diluting CRP standard solution (Scripps, cat. no. C0124, 2.37 mg/ml CRP) with dilution solution (50 mM Trizma base, 0.05% $NaN_3$, 0.9% NaCl, 0.5% BSA, 1 mM $CaCl_2*H_2O$, pH 7.7 with HCl). A 3.5-μL of sample was pipetted horizontally onto the porous film on the lid of the test strip (FIG. 1), where the sample dissolved the dried label. The strip was transferred into the measuring instrument into vertical position and the sample was allowed to incubate with the coated Si under the porous film for 5 min by shaking with the vibration motor located in the cover part of the measuring cell. After incubation the porous film with its frame was slided away from Si while the test strip moved into the washing/measuring cell. The cell was filled 4 times and aspirated 3 times with combined washing/measuring solution (50 mM $Na_2B_4O_7$, 0.1% $NaN_3$, 0.003% Tween 20, pH 7.9 with $H_2SO_4$). After the last fill, the ECL (f=10 Hz, Q=20 μAs, pulsing time 250 μs, 60 pulses, U=25 V) was measured with luminescence instrument described in U.S. Pat. No. 6,251, 690. After the measurement the cell was aspirated and the Si strip was removed. The cell was washed 3 times with draining fill before the next Si strip. The last fill was done with distilled water. The washing arrangement of the cell is shown in FIG. 4. The standard curve of CRP immunoassay is shown in FIG. 13.

Example 3

Figures 5A, 5B:
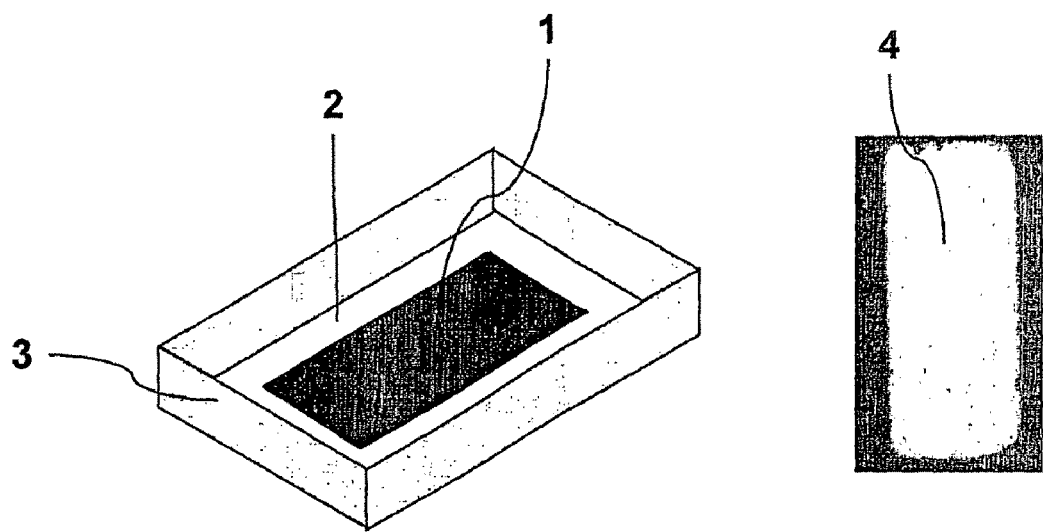
FIG. 5A: the silicon electrode is fitted to a conducting frame (3) with electrically insulating substance (2).
FIG. 5B: shows how luminescence (4) can be obtained from the whole area of the electrode.

Measurement of Tb-Chelate in the Measuring Cell Comprising of Anode Around Silicon Cathode In the experimental arrangement of FIG. 5A the silicon electrode was attached with tape to the bottom of the well and was filled up to the surface with UV-polymerizing adhesive (Loctite 322 or EPO-TEK OG 142). After the polymerization the tape was removed. The cell was filled with the washing/ measuring solution mentioned in Experiment 2, where the concentration of Tb chelate solution was $10^{-3}$ mol/l. ECL was measured (f=20 Hz, I=316 mM, pulsing time 500 μs, U=67 V) and photographs taken by a digital camera. Ten pulses were collected for obtaining the photograph. FIG. 5B shows that the luminescence is coming from the whole electrode area.

Example 4

Figure 6A:
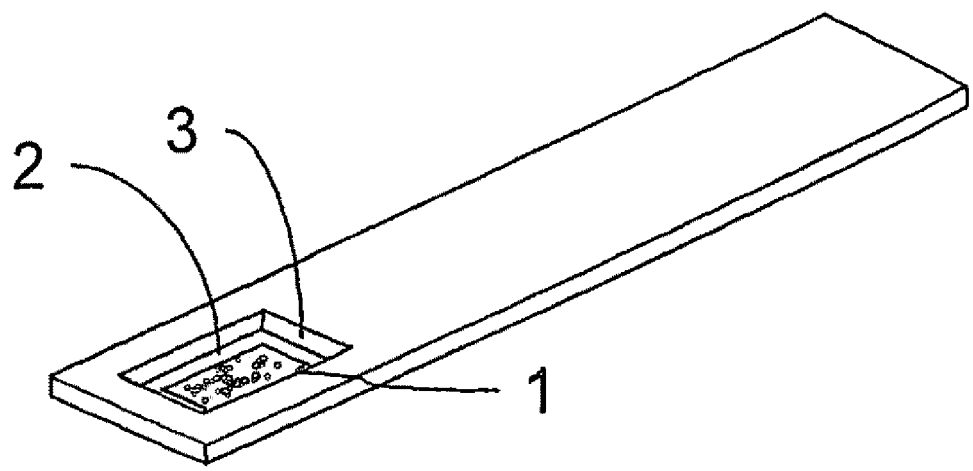
In FIG. 6A the test strip is viewed from the top and in FIG. 6B from bottom. The silicon electrode (1) is fitted to the test strip with electrically insulating substance (2). There is a direct electrical contact to cathode (1) and anode (3) from back side of the test strip.
Figure 6B:
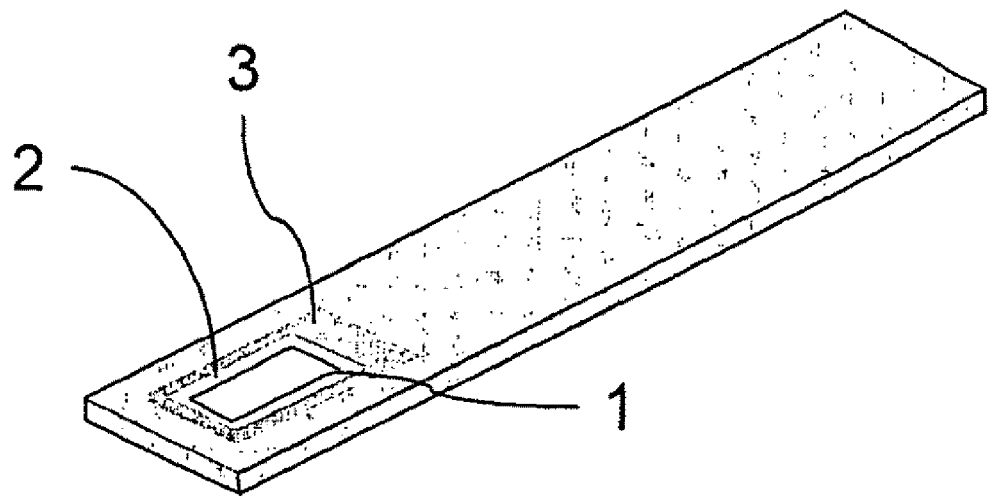
FIG. 6. Test strip.
Figure 7A:
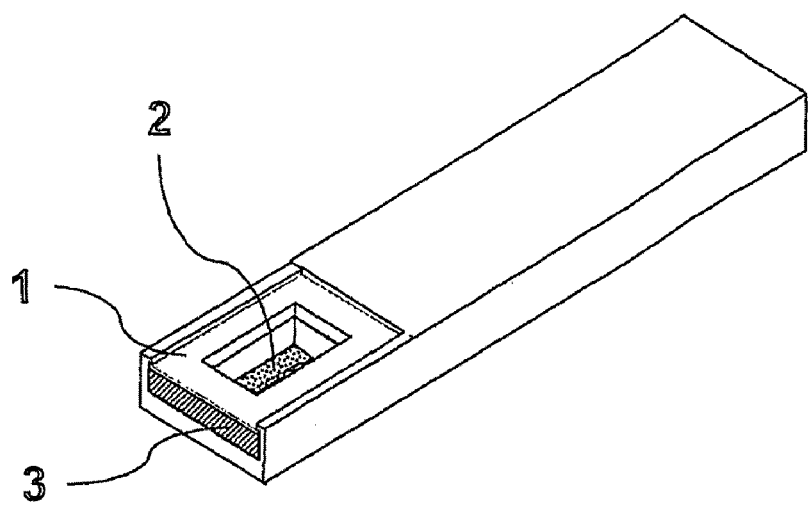
In FIG. 7A, the test strip is ready to use. On the bottom of the frame (1), a thin porous film (2) contains all the needed reagents in dry form. The porous film lies over the silicon surface but does not touch the electrode. A construction of elastic material (3) is inserted below the frame and it acts like a spring. When the sample is added onto the porous film (2), the sample dissolves the dry reagents. The reaction on the surface of the silicon electrode is started by pushing the frame down, when the porous film settles over the silicon and sample spreads over its surface. After a desired time, the frame (1) can be released from the down position and the reaction stopped.
Figure 7B:
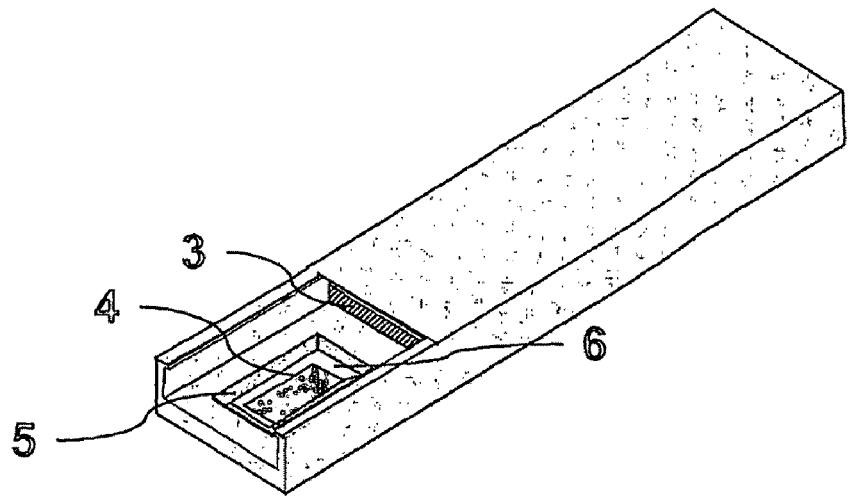
In FIG. 7b, the frame (1, 3) is pushed into the test strip after a fixed reaction time. The silicon electrode (4) is attached to test strip with electrically insulating material (6) and anode (5) functions at the same time as barrier of a low vessel.
Figure 7C:
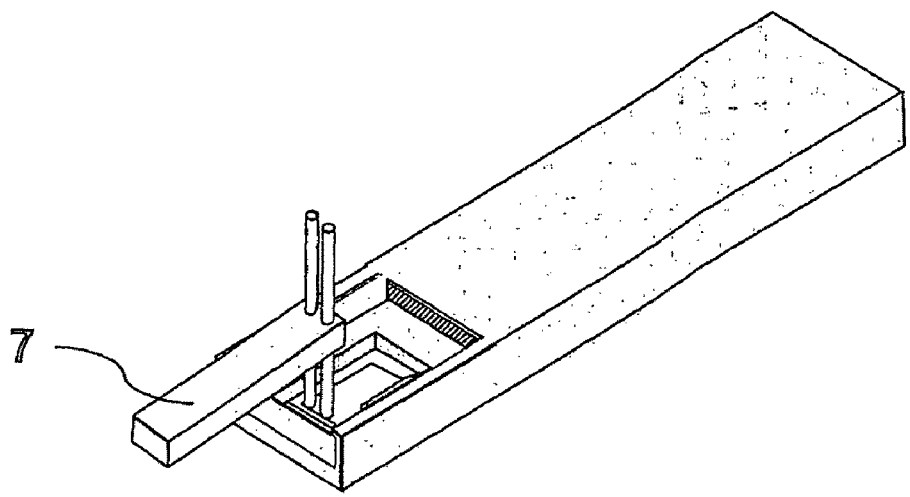
In FIG. 7C, the test strip is in washing step. With the washing arm (7) the silicon electrode is washed, if needed, before the measurement of ECL.
Figure 8:
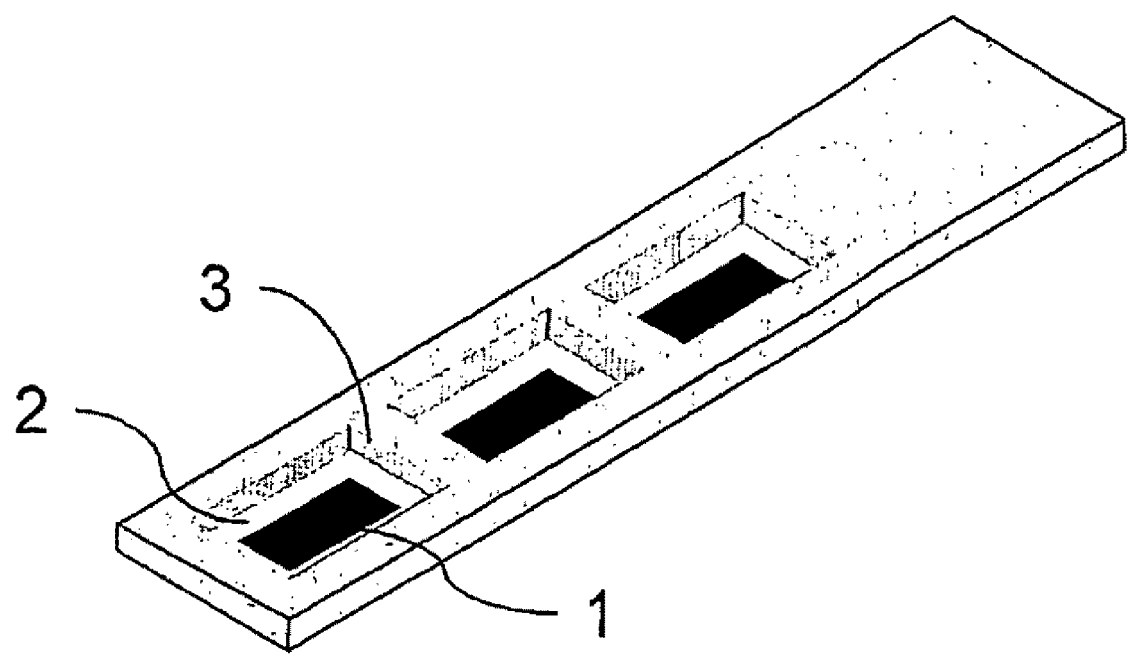
FIG. 8. Multiparameter test strip. Several reaction zones can be added to the test strip. Part of them can work as negative and positive controls.

The electrode unit of FIG. 3 can be attached to plastic basement facilitating easy electrical contact to both electrodes. The test strip is shown in FIGS. 6A and 6B. It can be built on the same principle also test strip in accordance with Example 2, which is shown in FIG. 7. Accordingly, by adding single electrode units to the strip it can be built test strip by which many assays can be performed simultaneously. Part of assays can work as negative or positive control. Such a test strip is shown in FIG. 8.

Example 5

Heterogeneous CRP Immunoassay with Serum Samples

Figure 14:
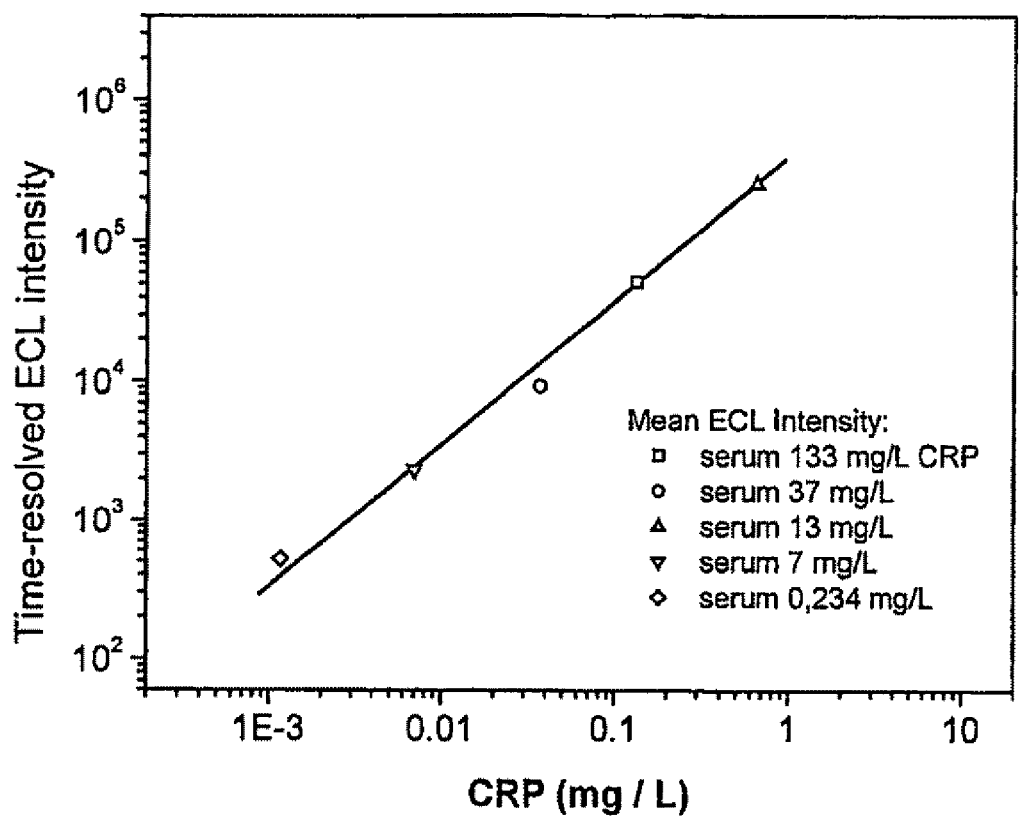
FIG. 14. Heterogenic hCRP immunoassay with serum samples. (see Example 3).

Known serum samples (measured turbidimetrically in an accreditated laboratory) with CRP concentrations of 133000, 37000, 13000, 7000, 234 ng/mL were measured by ECL immunoassay after diluting. The samples were diluted one hundred times with dilution solution (50 mM Trizma base, 0.05% $NaN_3$, 0.9% NaCl, 0.5% BSA, 1 mM $CaCl_2*H_2O$, pH 7.7 adjusted with HCl) and measured as shown in Example 2. The resulted serum sample curve is shown in FIG. 14.

Example 6

Homogeneous CRP Immunoassay with Standard Solutions

Figure 15:
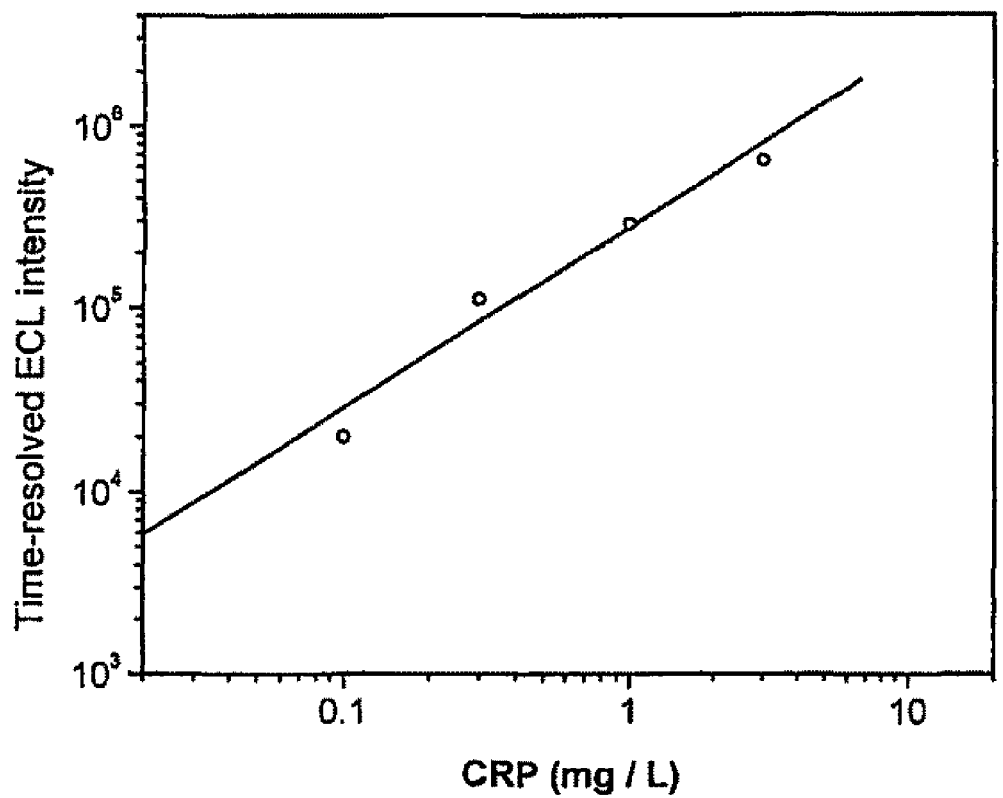
FIG. 15. Homogeneous hCRP immunoassay with standard sample solutions (see Example 4).

A homogeneous CRP immunoassay was performed by the CIPF-device based on ECL detection using standard solutions as in Example 2, with a modification that after incubation and after the test strip was pushed down into the measuring cell, there was no washing but the measuring cell was filled by a pump with measuring solution and the measurement was performed directly. The results of the homogeneous immunoassay are shown in FIG. 15.

Example 7

Heterogeneous TSH Immunoassay with Standard Samples

Heterogeneous hTSH immunoassay was done practically in the same way as shown in Example 2 with CRP. Test strip with Si-chips were prepared as in Example 1. The composition of antibody-coating solution of Si-chips was 0.1 M MES, 0.03 M $H_3BO_3$, 0.5 mM K-citrate, 0.025% glutaraldehyde, 0.05% bovine gamma-globulin containing 6.87 mg/mL of antibody (MIT0406 MOAB anti hTSH Medix Biotech Inc. USA) and that of saturation solution 50 mM Trizma base, 0.1% BSA, 0.1% $NaN_3$, 0.1% Tween 20, pH 7.5 adjusted with $H_2SO_4$. Also, the labeled antibody (Monoclonal anti-hTSH, clone 5404, 5.5 mg/mL, Medix Biochemica Oy Ab) which was labeled with Tb-2,6-bis[N,N-bis(carboksymethyl)aminomethyl]-4-bentsoylphenol chelate was dried to the porous film part of the test strip as described above.

Figure 16:
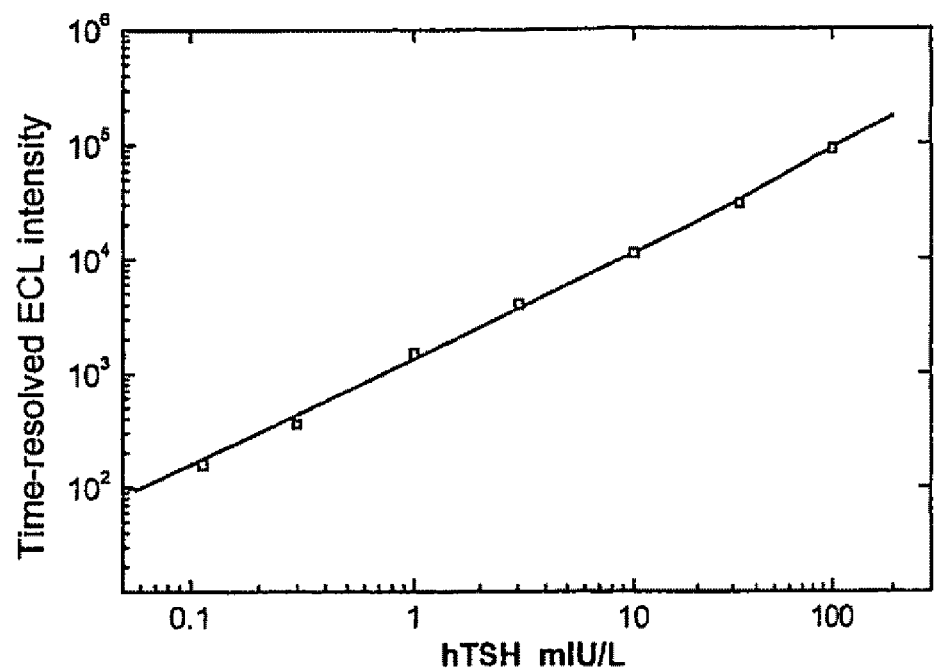
FIG. 16. Calibration curve of heterogenic hTSH immunoassay as measured by standard samples (see Example 5).

The standard samples (TSH concentrations 0.1, 1.0, 3.0, 10.0, 30.0, and 100.0 mIU/L) were prepared in test tubes by diluting TSH standard solution (Wallac, DELFIA hTSH kit, 324 mIU/mL TSH) with dilution solution (50 mM Trizma base, 0.05% $NaN_3$, 0.9% NaCl, 0.5% BSA, 1 mM $CaCl_2*H_2O$, pH 7.7 adjusted with HCl). Washings and the measurement were done as show in Example 2 except the incubation time was 15 min by continuous shaking. The standard curve of heterogeneous hTSH immunoassay is shown in FIG. 16.

Example 8

Heterogeneous Immunoassay of TSH with Serum Samples

Heterogeneous hTSH immunoassay was done practically in the same way as the CRP assay in Example 2. The Si-chips were prepared as in Example 1. The composition of the antibody coating solution of Si-chips was 0.1 M MES, 0.03 M $H_3BO_3$, 0.5 mM K-citrate, 0.025% glutaraldehyde, 0.05% bovine gamma-globulin containing 6.87 mg/mL antibody (anti-hTSH Medix Biotech Inc. USA) and that of saturation solution 50 mM Trizma base, 0.1% BSA, 0.1% $NaN_3$, 0.1% Tween 20, pH 7.5 adjusted with $H_2SO_4$. Also the labeled antibody (anti-hTSH, Medix Biochemica Oy Ab) which was labeled with Tb-2,6-bis[N,N-bis(carboksimethyl)aminomethyl]-4-bentsoylphenol-chelate was dried to the porous film of CIPF-device as shown above.

Figure 17:
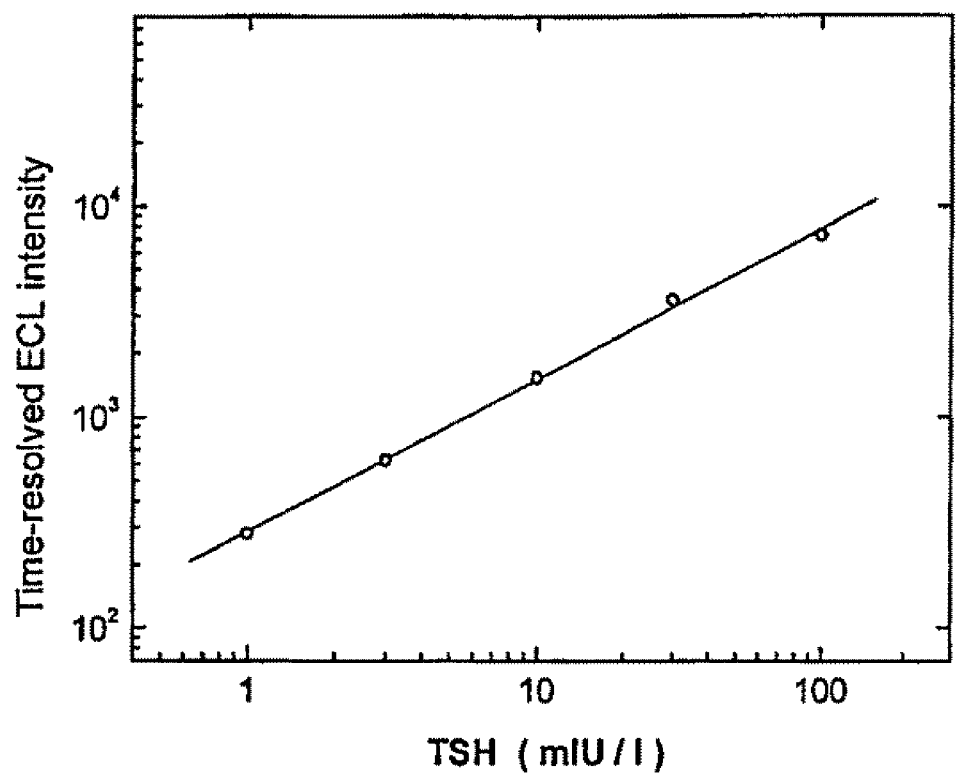
FIG. 17. Calibration curve of heterogenic hTSH immunoassay as measured with serum samples. hTSH-standards were prepared in serum (see Example 6).

The serum standards (TSH concentrations 1.0, 3.0, 10.0, 30.0, and 100.0 mIU/L) were prepared by diluting TSH standard solution (Scripps Laboratories, Inc., San Diego, USA) with serum. The serum TSH concentration was 0.45 mU/L. Washings and the measurement were done as shown in Example 2 except that the incubation time was 15 min with continuous shaking. The standard curve of hTSH immunoassay is shown in FIG. 17.

Example 9

Heterogeneous of TSH with Whole Blood Samples

Figure 18:
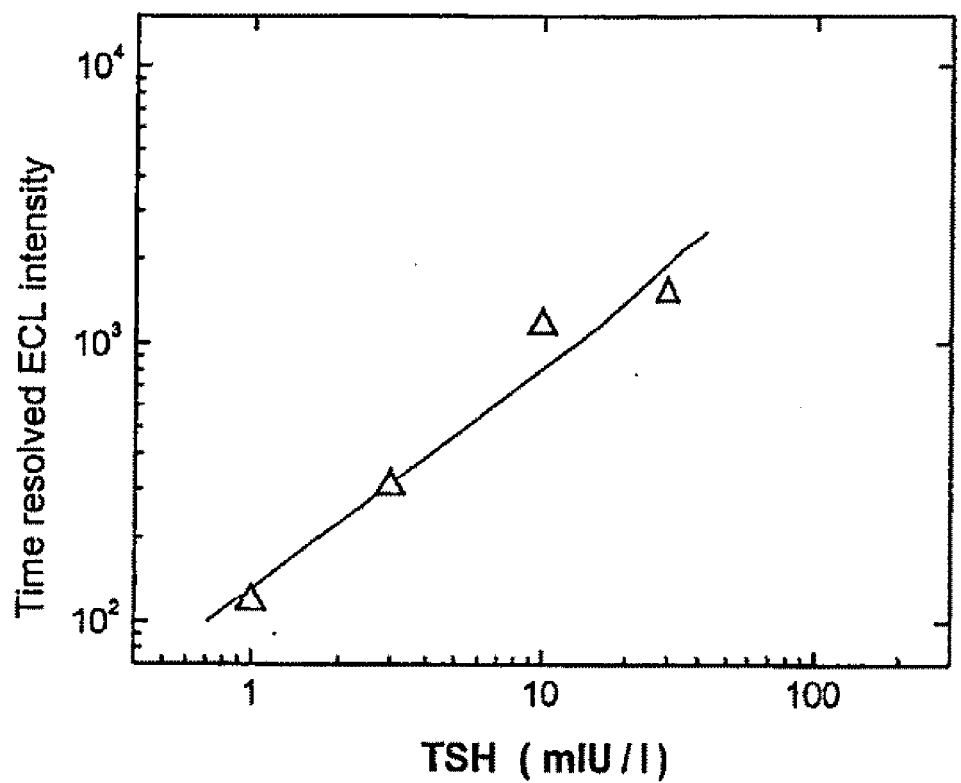
FIG. 18. Calibration curve of heterogenic hTSH immunoassay with whole blood samples. hTSH-standards were prepared in heparinized whole blood sample (see Example 7). The measurements were done using CIPF-device and luminescence reader (FIG. 9, Example 2).

Heterogeneous hTSH immunoassay was done practically in the same way as in Example 7. The whole blood standards (TSH concentrations 1.0, 3.0, 10.0, and 30.0 mIU/L) were prepared by diluting TSH standard solution (Scripps Laboratories, Inc., San Diego, USA) with heparinized whole blood. The TSH concentration of the whole blood was 0.5 mU/L. Washings and the measurement were done as in Example 5. The standard curve of the whole blood hTSH immunoassay is presented in FIG. 18.

Example 10

CRP Immunoassay on Antibody-Coated Nitrocellulose Porous Film Using Si-Cathodes Nitrocellulose porous film (7×4 mm, Schleicher & Schuell, 12 µm) was coated with anti-CRP antibody (101 g/mL) by incubating in buffer solution (50 mM Tris-HCl, pH 7.8, 0.05% $NaN_3$, 0.9% NaCl) at room temperature overnight. Thereafter the nitrocellulose was washed with saturation solution (50 mM Tris-HCl, pH 7.8, 0.05% $NaN_3$, 0.9% NaCl, 0.1% BSA, 6% D-sorbitol, 1 mM $CaCl_2$) and finally the porous film was kept in this saturation solution at room temperature overnight. After saturation, the porous film was dried over filter paper.

Figure 19A:
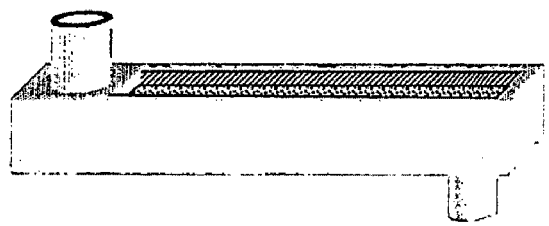
FIG. 19A describes a flow-through cell application of CIPF-device, where the affinity based reaction can be done on porous film or on silicon cathode.
Figure 19B:
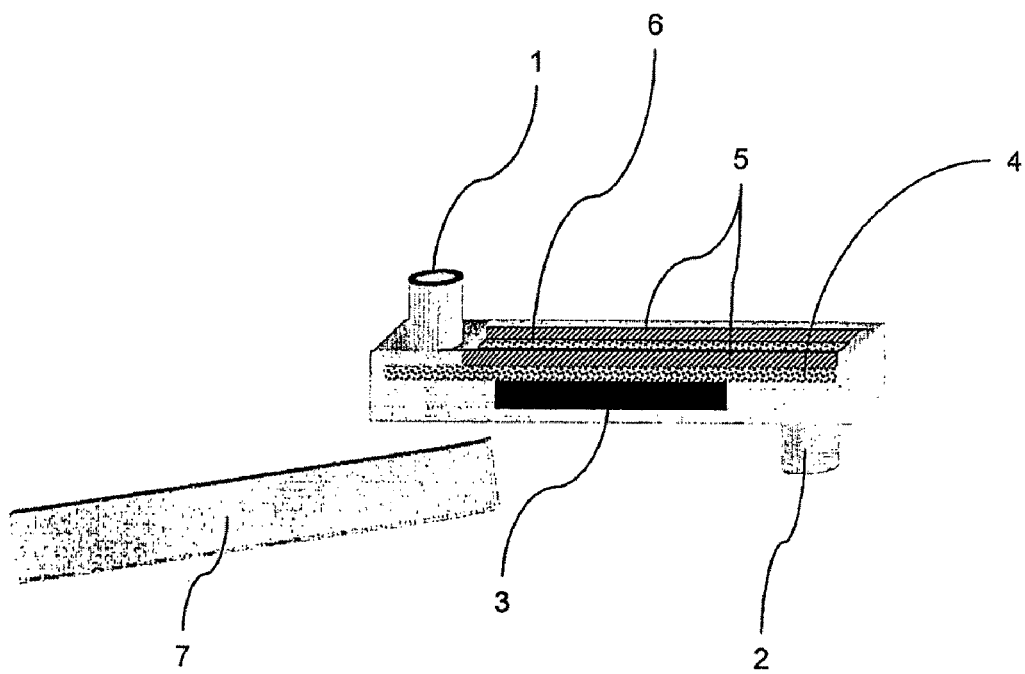
In FIG. 19B, the side (7) is detached so that the construction is visualizable. Porous film (4) acts as the transporter for liquid. Moreover, different reagents can be dried on it (e.g. labeled antibody). The measurement of ECL can be done directly through the porous film (4). The sample is added straight onto the porous film (4) enabling the immunoreaction to start. The liquid is added enough into the cell (6) that electrolytic contact between anode (5) and silicon electrode (3) is formed. The washing takes place through the inlet (1) and outlet (2) and the liquid moves along the porous film. A lid with a hole for addition of sample can be over the chamber (6).
Figure 20:
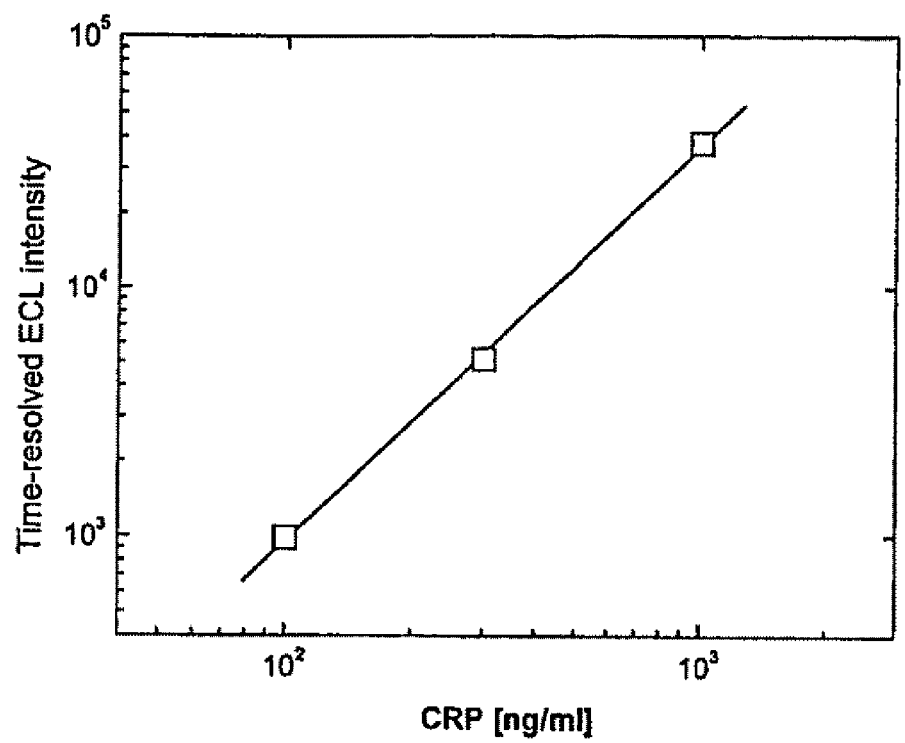
FIG. 20. A typical calibration curve of heterogenic hCRP immunoassay measured with a device shown in FIG. 15 (see Example 8).

The antibody coated nitrocellulose porous film was attached to the flow-through cell changed to the device (FIG. 19) and CRP standard 50 µL was added onto it. After incubation (5 min) the porous film was washed in the cell with 1 mL of wash/measuring solution (50 mM borate buffer, pH 7.9, 0.1% $NaN_3$, 0.003% Tween 20) and the with Tb chelate labeled antibody 50 µL was added onto it. After incubation (5 min) the porous film was washed with 1 mL of wash/measuring solution. After washing the ECL was measured in 500 µL of wash/measuring buffer (f=5 Hz, Q=20 µAs, pulsing time 250 µs, 500 pulses, U=34.8 V). A typical standard curve is shown in FIG. 20.

Example 11

Electrode Coating with Langmuir-Blodget (LB) Films and Molecular Examination of the Surfaces The experiment was performed with the ordinary Langmuir trough. The surface tension was measured with accuracy of 0.2 mN/m by Wilhelmy-plate method. The preparation of protein films were performed according to Nagagawa T. (1991) Thin Solid Films, 202, 151 and Owaku, K., (1989) Thin Solid Films 180, 61. The prepared protein films were transferred to electrode plates by the Langmuir-Shaefer method. The protein used in the coating was a monoclonal mouse antibody to hepatitis B surface antigen. LB films were formed to water/air boundary using Tris-HCl buffer (10 mM, pH 8.2) and alkylated polyethyleneimine (Aldrich, Germany).

Figure 21:
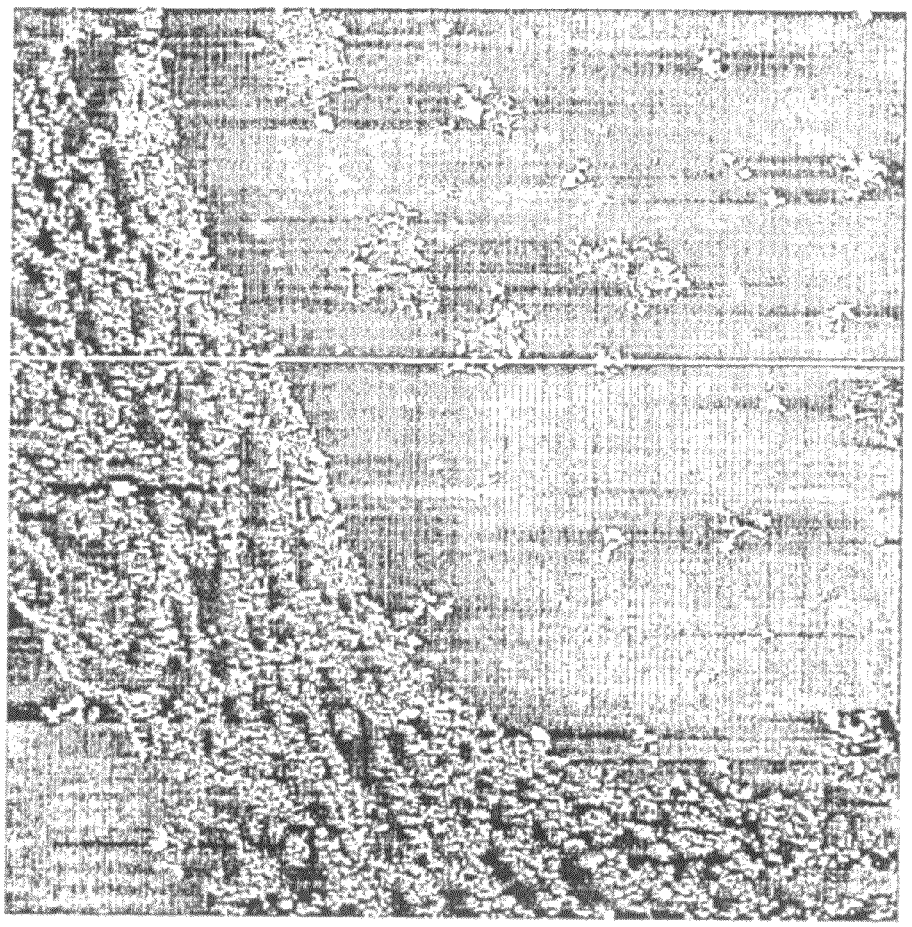
FIG. 21. AFM quality control image of coating of the Si chip by physical adsorption with antibody.
Figure 22:
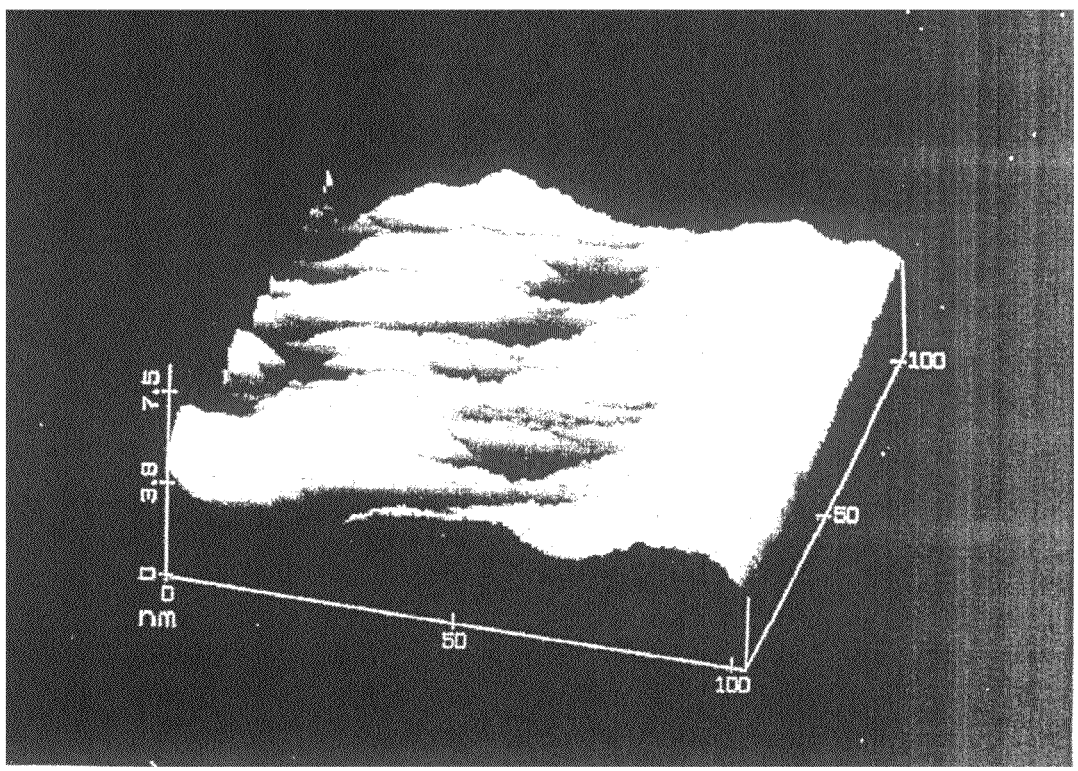
FIG. 22. Surface image of polystyrene obtained with the AFM measurement. The roughness of the surface prevents the effective use of AFM in the control of the coating (see Example 10).

Atomic force tunneling images of the LB coated surfaces were created with Nanoscope II FM instrument (Digital Instruments). The instrument works with constant current (tunneling) or constant deviation (atomic force). The pictures, which were stable at least 30 min, were registered by filtering and by 2D Fourier transform. Round patterns with size of 25×15 nm were observed that were identified as antibodies. The surface density was estimated to be $1 \times 10^{15}$ molecules/$m^{-2}$. Comparative results are shown in FIGS. 21 and 22.

The invention claimed is:

1. An electrochemiluminescent analytical device comprising:
    a working electrode of a material;
    a solid porous film on or adapted to be movable onto the working electrode; and
    a scaffold,
    wherein:
        the material of the working electrode is a conductor or a strongly doped semiconductor which is covered by an electrical insulator layer,
        the working electrode of the device is propped to the scaffold, through which the working electrode can be connected to excitation electronics of a luminescence measurement instrument,
        the working electrode serves as a cathode of the device,
        the solid porous film is liquid-permeable and of a thickness less than 100 μm, wherein the solid porous film is located in the vicinity of the working electrode, but not in direct contact with the working electrode,
    a free liquid junction of less than 100 μm exists between the working electrode and the porous film,
    the device being adapted so that a sample and other reagents to be brought onto the porous film and/or cathode can react with each other.

2. The device according to claim 1, wherein the cathodic working electrode is made of silicon or aluminum and the surface of the silicon or aluminum contains an oxide layer.

3. The device according to claim 1, wherein the thickness of the porous film on the working electrode is 1-20 μm and the porous film and working electrode are in contact through a solvent joint during a bioaffinity reaction and during a electroluminescence measurement.

4. The device according to claim 1, wherein either the surface of the working electrode or the porous film on the working electrode, or their assembly, is coated with bioaffinity molecules adapted to bind to the desired molecules to be analyzed.

5. The device according to claim 1, wherein specifically reacting molecules on the device are stored in the solid or amorphous state on surfaces of the device before a measurement process.

6. The device according to claim 1, wherein:
    the device is a test strip device,
    the working electrode forms a structural base of the test strip device,
    the working electrode and/or porous film is coated with a bioadsorbent,
    the porous film containing a dried labeled biomolecule is adapted to be brought in contact with the working electrode.

7. The device, according to claim 1, wherein the working electrode is coated with a porous film which is mechanically movable.

8. The device according to claim 2, wherein either the surface of the working electrode or the porous film on the working electrode, or their assembly, is coated with bioaffinity molecules adapted to bind to the desired molecules to be analyzed.

9. The device according to claim 3, wherein either the surface of the working electrode or the porous film on the working electrode, or their assembly, is coated with bioaffinity molecules adapted to bind to the desired molecules to be analyzed.

10. The device according to claim 2, wherein:
    the device is a test strip device,
    the working electrode forms a structural base of the test strip device,
    the working electrode and/or porous film is coated with a bioadsorbent,
    the porous film containing a dried labeled biomolecule is adapted to be brought in contact with the working electrode.

11. The device according to claim 3, wherein:
    the device is a test strip device,
    the working electrode forms a structural base of the test strip device,
    the working electrode and/or porous film is coated with a bioadsorbent, and
    the porous film containing a dried labeled biomolecule is adapted to be brought in contact with the working electrode.

12. The device, according to claim 2, wherein the working electrode is coated with a porous film which is mechanically movable.

13. The device, according to claim 3, wherein the working electrode is coated with a porous film which is mechanically movable.

14. The device, according to claim 1, wherein the electrical insulator layer has a thickness of 1-10 nm.

15. A method for analyzing a sample with an electrochemiluminescent analytical device, the device comprising:
    a working electrode of a material;
    a porous film on or adapted to be movable onto the working electrode; and
    a scaffold,
    in which device the material of the working electrode is a conductor or a strongly doped semiconductor, which is covered by an electrical insulator layer, the working electrode of the device being propped to the scaffold, through which the working electrode can be connected to excitation electronics of a luminescence measurement instrument, the working electrode serves as a cathode of the device, the porous film is liquid permeable and of a thickness less than 100 μm, wherein the solid porous film is located in the vicinity of the working electrode, but not in direct contact with the working electrode, the electrical excitation taking place at least 3 nm from the conductor,
    the method comprising:
    bringing a sample to be analyzed onto the porous film, and reacting the sample with other reagents brought onto the porous film and/or the cathode,
    applying excitation pulses to the reacted sample, wherein the reacted sample gives a luminescence signal; and
    analyzing the luminescence signal in relation to the amount of an analyte under concern.

16. The method of claim 15, wherein the thickness of the porous film on the working electrode is 1-20 μm and the film and the electrode are in contact through a solvent joint during the reaction and during the luminescence analysis measurement.

17. The method of claim 15, wherein the method comprises removing the porous film before for carrying out the luminescence analysis measurement.

18. The method of claim 15, in which:
the device is a test strip device;
the working electrode forms a structural base of the test strip device;
the working electrode and/or the porous film is coated with a bioadsorbent; and
the porous film contains a dried labeled biomolecule,
the method comprising:
bringing the porous film containing the dried labeled biomolecule in contact with the working electrode;
bringing a sample and/or a buffer solution onto the porous film to initiate a bioaffinity reaction;
allowing the bioaffinity reaction proceed;
stopping the bioaffinity reaction;
removing the porous film from the working electrode; and
making a measurement with an electroluminescence instrument.

19. The method of claim 17, wherein a primary mechanical force for moving the porous film is obtained from an elastic material.

20. The method of claim 18, wherein a primary mechanical force for moving the porous film is obtained from an elastic material.

21. The method of claim 15, wherein the electrical insulator layer has a thickness of 1-10 nm.

* * * * *